United States Patent [19]
Venton et al.

[11] Patent Number: 5,872,015
[45] Date of Patent: Feb. 16, 1999

[54] MOLECULAR DIVERSITY SCREENING METHOD

[75] Inventors: Duane L. Venton, Lombard; Charles P. Woodbury, Villa Park; Richard B. van Breemen, Elmhurst, all of Ill.

[73] Assignee: Board of Trustees of the University of Illinois, Urbana, Ill.

[21] Appl. No.: 645,968

[22] Filed: May 10, 1996

[51] Int. Cl.$^6$ .......................... G01N 33/537; B01D 63/00
[52] U.S. Cl. ................... 436/538; 210/321.63; 422/68.1; 435/7.1; 435/7.8; 435/287.2; 436/536; 436/824; 530/414
[58] Field of Search ....................... 210/321.63; 530/412, 530/413, 414; 435/7.1, 7.2, 7.8, 387.1, 207.2, 288.2; 436/536, 538, 86, 824; 422/68.1, 101

[56] References Cited

U.S. PATENT DOCUMENTS

| | | | |
|---|---|---|---|
| 4,082,668 | 4/1978 | Zeineh et al. | 210/321.63 |
| 5,023,987 | 6/1991 | Yau-Young | 424/450 |
| 5,136,025 | 8/1992 | Scheuermann et al. | 530/413 |
| 5,362,855 | 11/1994 | Garlick et al. | 530/385 |
| 5,412,087 | 5/1995 | McGall et al. | |

FOREIGN PATENT DOCUMENTS

95/12608  5/1995  WIPO.

OTHER PUBLICATIONS

Chemical Abstracts, vol. 125, No. 7, issued Aug. 12, 1996—Y.M. Dunayevskiy, et al. "Application of capillary electrophoresis–electrospray ionization mass spectrometry in the determination of molecular diversity." p. 641, col. 1, No. 81189t.

Chemical Abstracts, vol. 125, No. 15, issued Oct. 7, 1996—D. Horwell et al. "Targeted molecular diversity: design and development of non–peptide antagonists for cholecystokinin and tachykinin receptors," p. 34, col. 2, No. 184873r.

Chemical Abstracts, vol. 124, No. 12 issued Mar. 18, 1996—N. Porter, et al. "Technological development in high throughput screening: (1) Exploiting the molecular diversity of natural products, (2) Measurement of biomolecular interactions and the use of robotics," p. 708, col. 2, No. 155 943n.

Chemical Abstracts, vol. 116, No. 1 issued Jan. 6, 1992—W.J. Dower, et al. "The search for molecular diversity (II): recombinant and synthetic randomized peptide libraries," p. 313, col. 2, No. 3 161c.

Zuckermann et al, May 1992. Indentification of highest–affinity ligands by affinity selection from equimolar peptide mixtures generated by robotic synthesis. Proc. Natl. Acad. Sci USA 89: 4505–4509.

Thiesen et al, 1990. Target detection assay (TDA): a versatile procedure to determine DNA binding sites as demonstrated on SP1 protein. Nucleic Acids Research 18: 3203–3209.

Cohn et al, 1984. The use of antibodies to 5–bromo–2'–deoxyuridine for the isolation of DNA sequences containing excision–repair sites. J. Biol. Chem. 259: 12456–12462.

Wolfer et al, 1987. Protocols for use of ultrafiltration in determination of free ligand concentration and of complexity of ligand/protein interactions. Clin Chem 33: 115–117.

Chen et al, 1993. Pulsed ultrafiltration analysis of warfarin and phenlybutazone binding to human serum albumin. American Association of Pharaceutical Scientists Eigth Annual Meeting and Exposition. Pharaceutical Research 10:S–34, Abstract #APQ 1095.

Chen, S., "Pulsed Ultrafiltration Analysis of Compound/Macromolecule Interactions, " 206 *American Chemical Society Abstracts*, Chicago, IL (Aug. 1993). Abstract #Anyl 7.

Moos, W.H. et al., "Recent Advances in the Generation of Molecular Diversity" *Ann. Rep. In Med. Chem.*, 28:315–324 (1993).

Kaur, S. et al., "Identification of Specific Receptor Peptoid Ligands in Combinatorial Mixtures by Affinity Selection and Mass Spectrometry," *43rd ASMS Conference on Mass Spectrometry and Allied Topics*, Atlantic, GA (1995).

*Primary Examiner*—James C. Housel
*Assistant Examiner*—James L. Grun
*Attorney, Agent, or Firm*—Brinks Hofer Gilson & Lione

[57] ABSTRACT

A device and method is disclosed for the identification, concentration and isolation of a chemical compound from a mixture of compounds on the basis of the binding affinity of the chemical compound to a macromolecule or complex thereof, that is, to a receptor. Both the compounds to be assayed, and the macromolecules to which the compounds may bind, are free in solution. The method comprises contacting a mixture of compounds in solution with a solution of macromolecules or complexes thereof in a device possessing an ultrafiltration membrane to retain the receptor and bound compound receptor complex; washing through the device non-bound compounds; and releasing a bolus of the bound compound which passes through the ultrafiltration membrane where it may be analyzed chemically and/or spectrally (e.g. mass spectrometry) and/or bioassayed. The device includes a barrier such as an ultrafiltration membrane separating a binding chamber and an effluent chamber. An inlet port and wash port connect to the binding chamber. An effluent port connected to the effluent chamber is directed to analyzer equipment. Stirring means may be located within the binding chamber.

4 Claims, 15 Drawing Sheets

Molecular Diversity Screening System

Molecular Diversity Screening Device - Concentric Shaft

Molecular Diversity Screening Device - Wobble Shaft

Molecular Diversity Screening Outcome

3D Sample Multiplexing

Molecular Diversity Screening Device Elution Characteristics

Binding and Release of EHNA from Adenosine Deaminase

Selection and Release of EHNA from a Library Using Adenosine Deaminase

Solution-phase Synthesis of a 7-Membered EHNA Library

R = $nC_6H_{13}$; $nC_7H_{15}$; $nC_8H_{17}$; $nC_{10}H_{21}$;

(CH3)2CHCH2; (CH3)2C=CHCH2; PhCH2

TMBS: Trimethylbromosilane
DMAC: N,N-dimethylacetamide

Solution-phase Synthesis of a 7-Membered EHNA Library

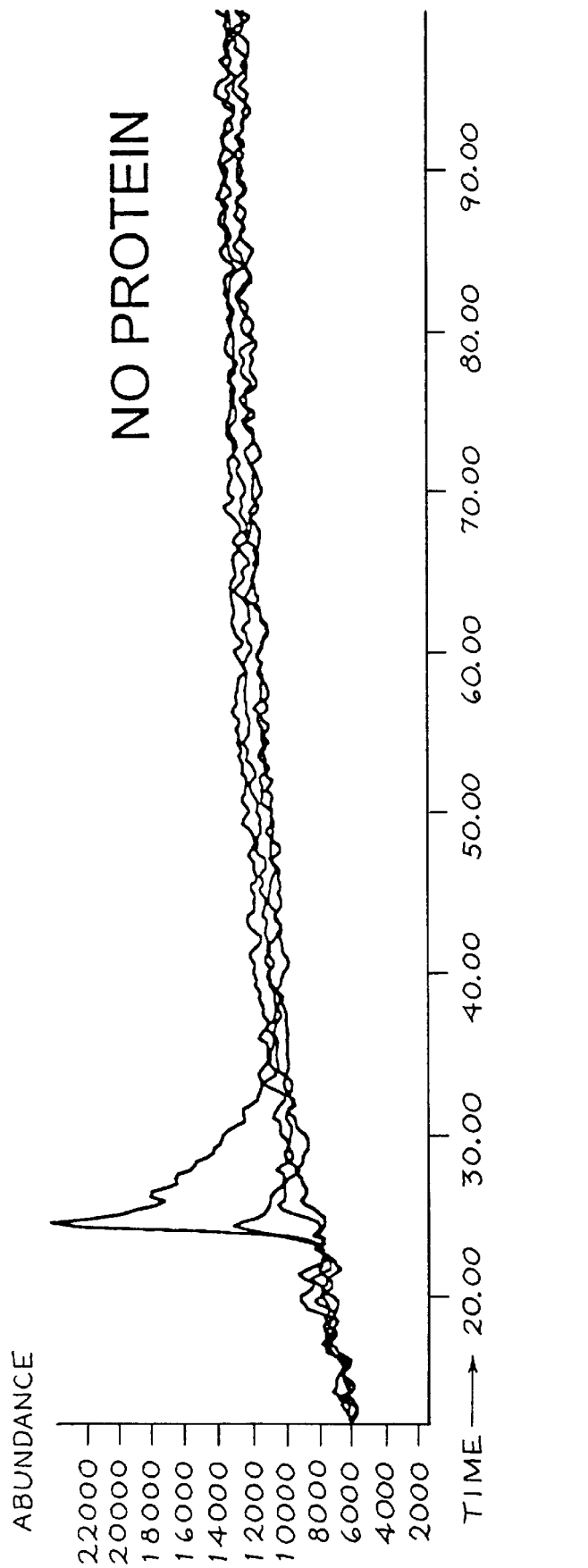

EHNA Analog Screen

EHNA Analog Screen

Congo Red Analogs

MOLECULAR DIVERSITY SCREENING METHOD

BACKGROUND

The invention relates to a device and method for screening molecularly diverse chemical mixtures such as combinatorial chemical libraries and natural products for substances which bind with affinity and specificity for a macromolecule (a receptor) or complex thereof. The device employs ultrafiltration of compounds in solution to identify, concentrate and isolate candidate compounds that bind to the receptor.

The selection and identification of pharmacologically active molecules directly from compound mixtures called combinatorial libraries is an approach to drug discovery and lead optimization that is cost effective compared to testing individual molecules singly.

Small organic molecules that possess unique spatial and thermodynamic properties which allow them to bind specifically to biologically related macromolecules and their complexes are candidates for therapeutic drugs. Examples of the macromolecules include proteins, DNA, RNA, viral particles and whole cells. The binding of these compounds to such macromolecules can transiently or permanently eliminate or activate the function of those macromolecules. Thus, a compound which binds to and eliminates the function of a coat protein of a virus could serve as an effective pharmacologic agent against that virus. Similarly, a compound which binds to and activates a receptor for estrogen could serve as a useful active agent for estrogen replacement therapy.

In the classical approach to drug development, single compounds are individually synthesized and tested for a given biological activity. Consequently, a one-to-one correlation between the single chemical structure and biological activity is maintained. However, because both the synthesis and bioassays are very labor intensive, this approach is inefficient and expensive. The pharmaceutical industry has recognized the significant enhancement in efficiency that may be gained by simultaneously producing many compounds, called chemical libraries, and testing them as a group. Numerous methods have been developed for the preparation of complex chemical libraries containing considerable molecular diversity (Moos, 1993). A difficult challenge has been the screening of these libraries to detect molecules with a desired biological activity or binding profile that is specific for a given target receptor. The difficulty comes from the fact that although complex mixtures can be assayed and a given biological activity or binding can be determined to be present in the mixture, the identity of the molecule(s) responsible for the given activity or binding is not known.

An essential aspect of screening combinatorial libraries is the ability to identify the active components in these large mixtures, usually based on the strength of binding to a selected macromolecule. Common approaches to this problem utilize a) immobilization of either the target or library molecules on a solid phase support to facilitate identification of the active compounds in the library, or b) iterative resynthesis of components of the library until a single active compound is identified. However, immobilization alters the affinity characteristics of the bound species, and the resynthesis approach is labor intensive and time consuming.

One strategy to identifying drug candidates has been to prepare the chemical compounds in a library covalently linked to specific areas on a surface. In this technique, the use of photochemically labile protecting groups allows the light-directed, spatially addressable, parallel, chemical synthesis of thousands of compounds at defined sites on a microchip. (McGall, 1995; Stryer, 1991) Compounds which bind a specific receptor are then identified by bathing the chip with a solution of the receptor and, through various means, identifying the location of the bound macromolecule on the chip. The structure of the compound which binds the given macromolecule is identified by location on the chip. Similar approaches synthesize compounds bound to individual pins or beads, which are then assayed by evaluating which bead or pin binds the macromolecule. (Lam et al., 1991; Geysen, H. M. et al., 1984) Molecular biological approaches include having a compound, typically a peptide, tethered to a surface, i.e. a phage particle. (Smith, *Science*, 1985)

The majority of the available methods to screen drug candidates require the compounds under investigation to be covalently linked to the given surface in order to define the relationship between structure and activity or affinity for the macromolecule. It is well understood in the industry that such attachments chemically alter the compounds and can result in both false positive as well as false negative results. Consequently, these approaches are of limited use.

Alternatively, for assay purposes, individual compounds can be released into solution from the macromolecular surfaces on which they are bound. Several coding methods have been developed to relate chemical structure to a particular surface from which a compound has been released. However, all of these strategies remain labor intensive.

A general approach to reducing the number of analyses which must be preformed to relate a particular physical property, e.g. spectral property, biological activity, to a given chemical structure uses indexed libraries (referred to in the more general sense as sample multiplexing). This technique can be used to help reduce the number of assays which must be performed in screening libraries by any of the present methods. This approach involves preparing two series of sublibraries. (Smith et al., 1994; Pirrung, 1995) The sublibraries are tested as a matrix whose column and row intersections serve as indices for a unique structure in the sublibraries. (Woodbury et al., 1995) Although this approach reduces the labor in bioassaying the compounds, the number of assays (equal to $2\sqrt{n}$ where n is equal to the number of compounds in the libraries) remains large for large libraries. Further, when more than one compound in the library is active, such indexing may not give a unique solution to the relationship of structure and activity.

A major obstacle toward identifying new candidates for drug development is that, although many methods have been developed to prepare mixtures of chemically diverse compounds, the screening of these mixtures is inefficient and labor intensive. There is, therefore, a need for methods (assays) which allow for rapid and efficient screening of large numbers of compounds for those having specific binding characteristics. A useful system would provide for the screening of compounds for binding to macromolecules and their complexes in which there is no need to bind to a surface. Another goal is to preserve quantities of difficult to obtain macromolecules such as recombinant proteins. The system should include conditions where structural information on the bound specific compound is obtainable through operation of the assay.

SUMMARY OF THE INVENTION

The present invention provides a device and a method which concentrates the specific compound(s) of interest on a defined concentration of a receptor molecule (target) which is free in solution in the device, and then releases the bound compound(s) by methods which perturb the binding of the specific compound(s) after the other compounds in the mixture have passed through the device. In this manner, and in a single experiment, specific compound(s) are selected and separated from the mixture while both receptor and compound mixture remain in solution. Thus, specific compounds that bind to a target macromolecule are separated from very large numbers of non-specific compounds in a single step and then released and analyzed in isolation. There is no need to attach molecules to a surface, large number of candidate compounds can be screened in one step, the test compounds are concentrated, sensitivity is increased because there is no surface area limitation, and both the receptor and compounds are allowed to act in their native state.

The present invention is directed toward a device and method satisfying the need for screening a large mixture of chemical compounds for specific compounds that bind a preselected, target macromolecule. As used herein, the macromolecule to which the compounds being assayed will be applied is the "receptor." The device has a defined internal shape and volume which concentrates the specific compound(s) of interest on a defined concentration of receptor in the device and then releases the compounds by methods which perturb the specific compound(s) binding after the other compounds in the mixture have passed through the device. In this manner, specific compound(s) are selected and separated from the mixture while both receptor and compound mixture remain in solution. The released compounds are then subjected to spectral, biological or other analyses. Because large amounts of the receptors are difficult to obtain, in particular receptors produced by recombinant technology, an aspect of the invention that is advantageous is that the target macromolecules are retained by a barrier within the device and may be reused in subsequent assays, thereby conserving the macromolecules.

A full showing of pharmacologic utility of a single specific compound isolated from a large, random population of compounds involves the following steps: (1) generation of the library of compounds, (2) demonstration that a particular compound binds specifically to a receptor associated with a particular physiological function, (3) isolation of the specific binding compound, (4) determination of the structure of the specific binding compound, (5) large-scale synthesis of the specific binding compound, (6) demonstration of biological activity of specific compound, and (7) pre-clinical and clinical testing. Although methods currently exist for steps (1) and (4)–(7), the device and method of the present invention provides a novel approach to steps 2 and 3.

A method of the present invention for identifying chemical compounds present in a mixture of compounds which bind to a predetermined target macromolecule comprises: (a) contacting a solution of the mixture of compounds with a solution of macromolecule or complex thereof under conditions that allow formation of a bound compound for those compounds having affinity for the macromolecule or complex thereof; (b) allowing non-bound compounds to separate from the bound compounds; (c) releasing the bound compounds in the mixture from the macromolecule or complex thereof, (d) isolating the released compounds from the macromolecules or complexes thereof; and (e) identifying the isolated compounds.

An embodiment of the present invention is an ultrafiltration device for identifying compounds present in a mixture of compounds which bind to a predetermined target receptor. The device includes a binding chamber formed from an ultrafiltration membrane sandwiched between a lower assembly defining an inlet chamber and an upper assembly defining an outlet chamber, a stirring means disposed within said inlet chamber, and an analyzer in fluid communication with the outlet chamber. The ultrafiltration device optionally includes a stirring means that comprises an orbital angularly deflecting disc.

An embodiment of the molecular diversity screening device of the present invention utilizes as a barrier an ultrafiltration membrane to retain a target receptor or its complex while allowing smaller compounds to pass through. The device includes an ultrafiltration membrane that separates a binding chamber and an effluent chamber. An inlet port and a wash port are in communication with the binding chamber. An effluent port is in communication with the effluent chamber. Preferably, a shaft is connected to a rotating head located in the binding chamber to mix the contents of the chamber. In another embodiment, the shaft is fixed and orbits around the axis of rotation to provide increased mixing.

Under specific conditions of receptor concentration, chamber volume, membrane surface area, and binding environment, set forth herein in the Description of the Preferred Embodiments, compounds having affinity for the receptor or its complex while free in solution are bound to the receptor and retained, while non-bound compounds pass through the device. After the non-bound compounds pass through the device, the receptor or its complex in association with the bound compound is perturbed by a destabilizing environment causing the compound to be released from the receptor and eluted from the chamber, while the macromolecule (receptor) is retained for repeated use. Examples of destabilizing environments are changes in pH, ionic strength, organic solvent, denaturing agent, temperature or competing agent. Preservation and reuse of receptors is advantageous because it is difficult to obtain large amounts of many biologically important macromolecules.

This flow-through binding system, called a molecular diversity screening system, permits the identification and characterization of high affinity ligands within combinatorial libraries during a single experiment while maintaining both the ligand mixture and macromolecular receptor free in solution. An aliquot or ligand or combinatorial library, is injected and pumped through a molecular diversity screening device containing a solution-phase receptor that is trapped by a barrier, e.g. an ultrafiltration membrane. High affinity ligands bind and dissociate from the solution-phase receptor causing their elution profile from the ultrafiltration chamber to be altered.

Under specified conditions of compound and receptor concentration, volume of the binding chamber and surface area of the ultrafiltration membrane, very dilute solutions of compound (femtomolar) can be passed through the device with retention of a majority of specific compound. Therefore, the device and method can be used to concentrate as well as to select specific compounds from complex mixtures. The device and method effectively separate and concentrate a compound in the complex mixture which has affinity for the receptor or complex thereof. High sensitivities are attainable because of the ability to concentrate the bound specific compound and wash out those not bound.

The effluent from the device may be passed to an attached, chemical, spectral, or biochemical analyzer, for example a mass spectrometer, which provides structural and biological information on a specific compound in the mixture which binds the chosen receptor. Thus, the device effluent may be used in conventional bioassays to define the biological activity of that specific compound in the mixture which binds the chosen receptor or complex thereof. An aspect of the invention is to provide a means for inexpensive and rapid isolation and identification of compounds which specifically bind to a given receptor or complex thereof, as well as to provide structural information on the specific compounds that bind.

Another aspect of the invention is to provide a method for screening specifically bound compounds for a particular biological activity related to the receptor to which the specific compound is bound. Another aspect of the invention is to provide a means for screening a large library of chemicals for the presence of specific compounds which bind to different biologically important receptors in a molecular complex, whose properties are different than the same molecules in isolation.

Many different types of compound libraries may be screened by the molecular diversity screening system. Among these types of libraries are those derived from various polymers such as peptides, oligonucleotides, phosphorothioate oligonucleotides, oligo- and polysaccharides, peptidomimetics, and "peptide" nucleic acids or PNAs. In addition, chemical libraries of nonpolymeric small organic molecules using solid phase synthesis can be tested after release from the polymer. Importantly, the invention can also be applied to small organics produced free in solution. Further, molecular diversity from plant or marine sources may be screened by the invention.

Another aspect of the invention is to provide specific binding compounds of defined chemical structure which, having been identified by the methods of the invention, are readily produced by standard synthetic means.

Definitions:
chemical compounds: typically the invention is used to screen small organic molecules (referred to as chemical compounds, characterized as generally having a molecular weight of about 100–1000 daltons) which bind to macromolecules, e.g. proteins, DNA, RNA etc. or complexes thereof. However, the system may be employed with any set of compounds differing in molecular weight by about 700 atomic mass units, and which can be separated by an ultrafiltration membrane.

library: a collection of chemical compounds ultrafiltration membrane: a permeable barrier or membrane, as used herein, that functions to retain macromolecules and permit smaller chemical compounds to pass through macromolecule: a molecule which is capable of binding to a chemical compound [see definition of chemical compounds]

receptor: a molecule to which compounds to be tested are applied to determine binding affinity.

BRIEF DESCRIPTION OF THE DRAWINGS

FIGS. 11A–11C are EHNA analog screens.

DESCRIPTION OF THE PREFERRED EMBODIMENTS

A device and method are provided for screening molecularly diverse chemical mixtures (chemical libraries, natural products) for substances which bind with affinity and specificity (herein referred to as specific compounds) for a receptor or complex thereof, and are thus potentially useful for pharmacologic or other purposes. The device and method further provide for the generation of analyzable quantities (picomole to millimole) of such specific compounds and a means to, in part, define their structures.

Figure 1:
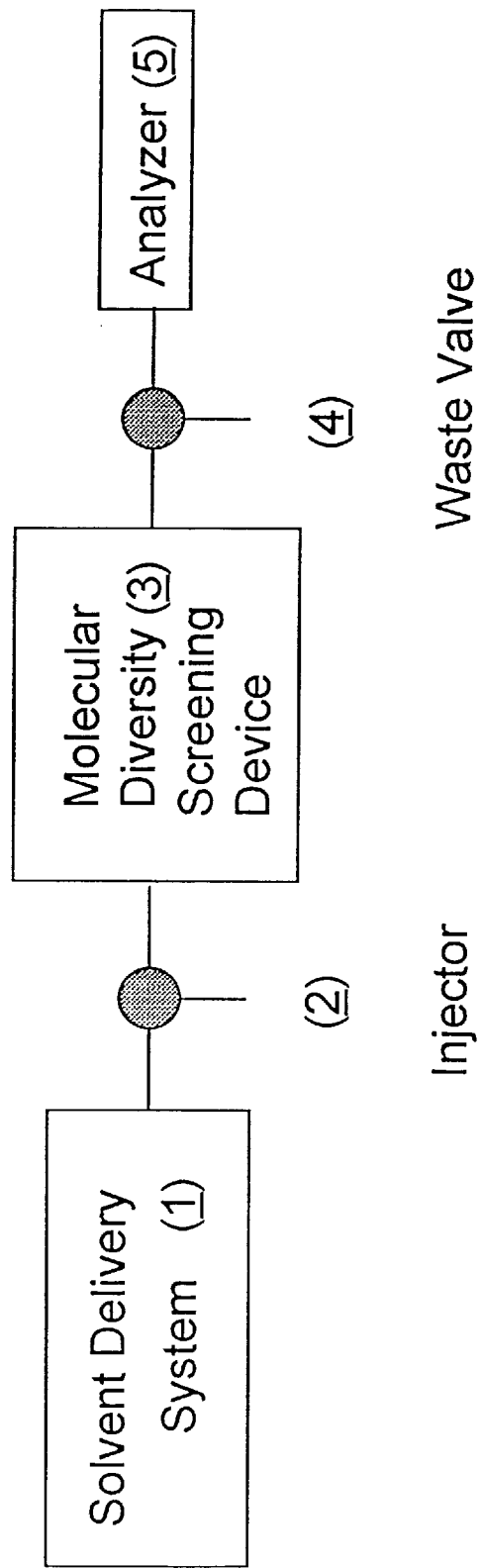
FIG. 1 is a schematic flow chart of a molecular diversity screening system.

Referring to FIG. 1, the system for screening a chemical library includes a solvent delivery system 1, an injector 2, a molecular diversity screening device 3, a waste valve 4, and an analyzer 5 with data analysis capabilities. The solvent delivery system 1 and injector 2 include accessory pumps, tubing and measuring devices to deliver precise aliquots of receptors, chemical library solutions, solvents and buffers, and the like to the screening device 3. The waste valve 4 is used for bypassing fluids away from the analyzer 5. The analyzer 5 may include any type of chemical, spectral and bioassay devices, but is not limited to: a mass spectrometer, ultraviolet detector, diode array detector, infrared detector, nuclear magnetic resonance detector, electrochemical detector, amino acid analyzer, peptide sequencer, nucleotide sequencer, or any type of bioassay procedure or device.

Figure 2:
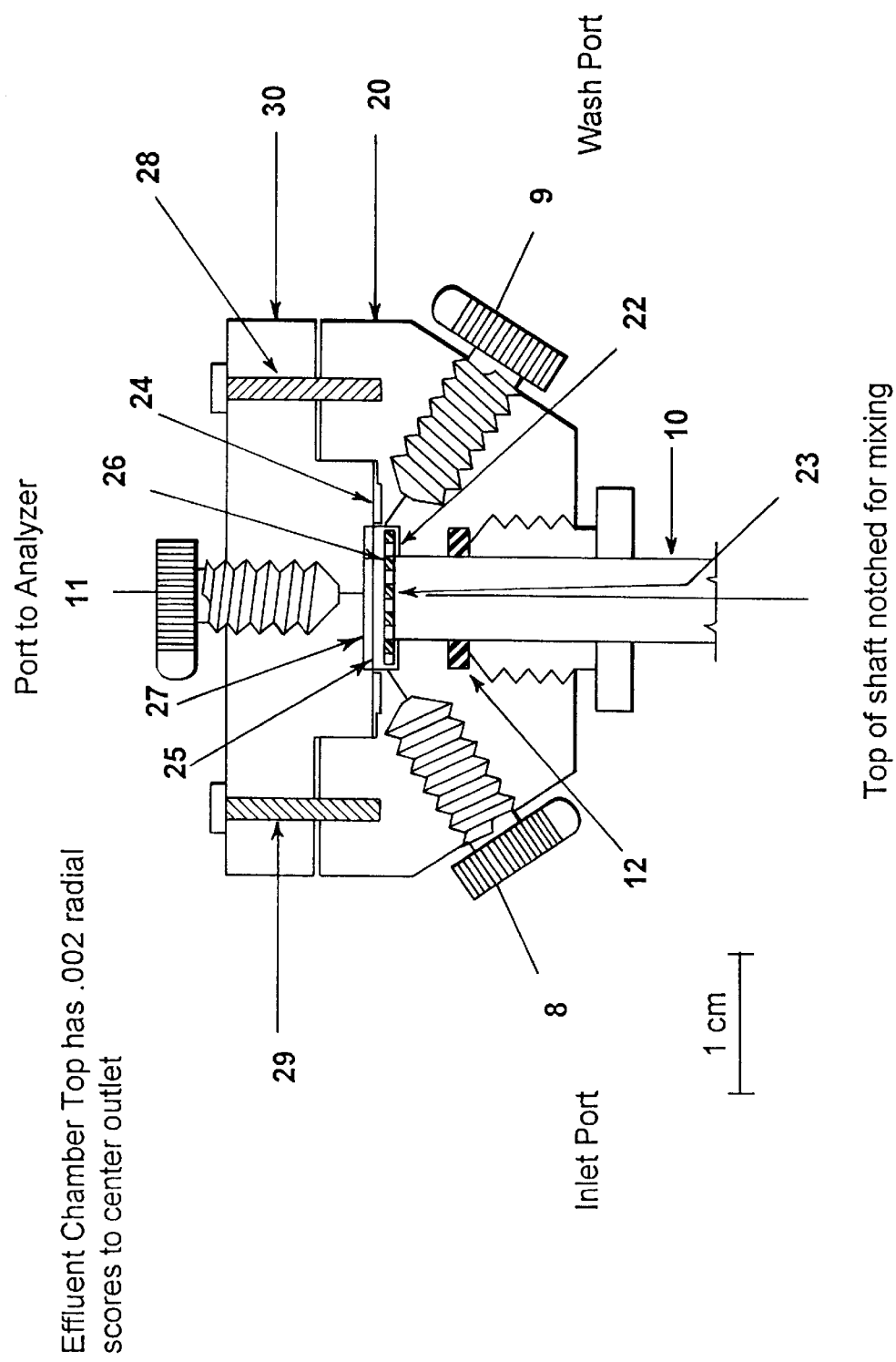
FIG. 2 is a sectional view of an embodiment of the molecular diversity screening device.

Referring to FIG. 2, the device includes an upper assembly 30 and lower assembly 20 which seals an ultrafiltration membrane 25 so as to create two chambers, a binding chamber 26, and an effluent chamber 27. In the binding chamber there are two ports, one capillary inlet port 8 for introducing receptors, reagents and libraries, and a wash port 9 for removing receptors and other macromolecules. In the depicted embodiment, the binding chamber 26 is stirred by a rotating shaft 10 and disc 22. In an alternate embodiment (not shown), the binding chamber is not stirred. The effluent chamber 27 also has a port 11 which directs effluent passing through the ultrafiltration membrane to the analyzer 5 and data system.

The components of the screening device are preferably made from material that is unreactive, or bio-compatible, with the target receptors, compounds to be screened and other solutions used in the device. For example "Polysulfone" is one such material that may be used with a wide variety of chemicals and biological materials because it is relatively inert. Also, this material is easy to machine to the desired chamber geometry. Other useful materials may include "TEFLON®," "PEEK," and "LEXAN®," to name a few.

As shown in FIG. 2, the lower assembly 20 has a binding chamber 26, inlet port 8, wash port 9 and bores for the stirring shaft 10 and assembly bolts 28 and 29. A seal 12 is provided to minimize fluid leakage past the shaft 10. A chamber seal 24 is also provided to prevent leakage past the ultrafiltration membrane 25 out of the binding chamber 26 or around the membrane 25 into the effluent chamber 27. The binding chamber 26 has a cylindrical geometry to allow stirred circulation of the contents minimizing dead spaces and corners where receptors may accumulate. The depth of the chamber is sufficient for placement of a stirring disc 22 with minimal clearance between the disc and the chamber walls and ultrafiltration membrane to minimize the active binding chamber volume. The stirring disc 22 has a plurality of radial notches 23 on its peripheral edge to increase the agitation and shear forces attained with its rotation.

The upper assembly 30 has an effluent chamber 27, an effluent port 11 and bolt holes for the assembly bolts 28 and 29. The upper assembly is machined to mate with the lower assembly 20 and seal the ultrafiltration membrane 25 therebetween. The effluent chamber 27 should have a minimal volume. In one embodiment, to minimize chamber volume, the effluent chamber is made up of a series of concentric circular channels with radial channels intersecting the circular channels and leading to the effluent port 11. The channels may be between about 0.002 and 0.015 inches deep. The concentric rings formed between the channels support the ultrafiltration membrane against the differential pressure across the membrane. It is believed that the pressure in the binding chamber side of the membrane may be as high as 70 P.S.I. during normal operation, depending upon the membrane and analyzer equipment selected, but should not be greater than that recommended by the membrane manufacturer.

The ultrafiltration membrane 25 may be any commercially available ultrafiltration membrane, such as from Amicon or Millipore. In the following examples, an ultrafiltration membrane having a molecular weight cut-off of 10,000 available from Amicon was used. The pore size or molecular weight cut-off size selected may depend on the size of the compounds being screened and the size of the receptor molecules being used.

As mentioned above, it is desirable to use a small binding chamber 26. The actual volume of the chamber must match the sensitivity of the analytical equipment to be used. Small chambers can be used with more sensitive analyzers. For example, a binding chamber volume of 100 $\mu$L may be sufficient as disclosed for the Examples discussed below. On the other hand, if stirring mechanisms are to be used, the volume may need to be greater to accommodate the stirring mechanism.

Although the screening device functions well without stirring mechanisms, the device may incorporate a number of means to stir the contents of the binding chamber. For example, magnetic, mechanical, hydrodynamic or ultrasonic means are contemplated to accomplish the stirring, mixing or agitation of the contents of the binding chamber. For example, a magnetic stirring bar (not shown) could be placed in the binding chamber 26 and the screening device placed on a magnetic stirrer to magnetically couple and control the stirring. It is believed that spinning the bar at about 60 R.P.M. provides adequate mixing of the chamber contents. One drawback to this method of stirring is that it requires a larger volume in the chamber to accommodate the bar. To maintain high membrane flux rates and attain the desired pulsed ultrafiltration characteristics, it is desirable to maximize the membrane surface area to binding chamber volume ratio. For example, it is contemplated that a membrane may cover a 10 mm diameter binding chamber that has a volume about 100 $\mu$L.

In the embodiment shown in FIG. 2, the stirring is accomplished by means of a rotating shaft 10 coupled to a stirring disc 22. The stirring disc 22 has radial notches 23 at the peripheral edge. Use of the stirring disc 22 permits a smaller active binding chamber volume, by which it is understood to mean the fluid capacity of the chamber with the stirring disc in place. It is believed that higher stirring R.P.M.'s may be used with this embodiment, as compared to the above described magnetic stirring bar. Nonetheless, too high a stirring speed may cause severe shear forces in the chamber that could alter the native state of the macromolecules and dislocate high affinity ligands from the receptors.

Figure 3:
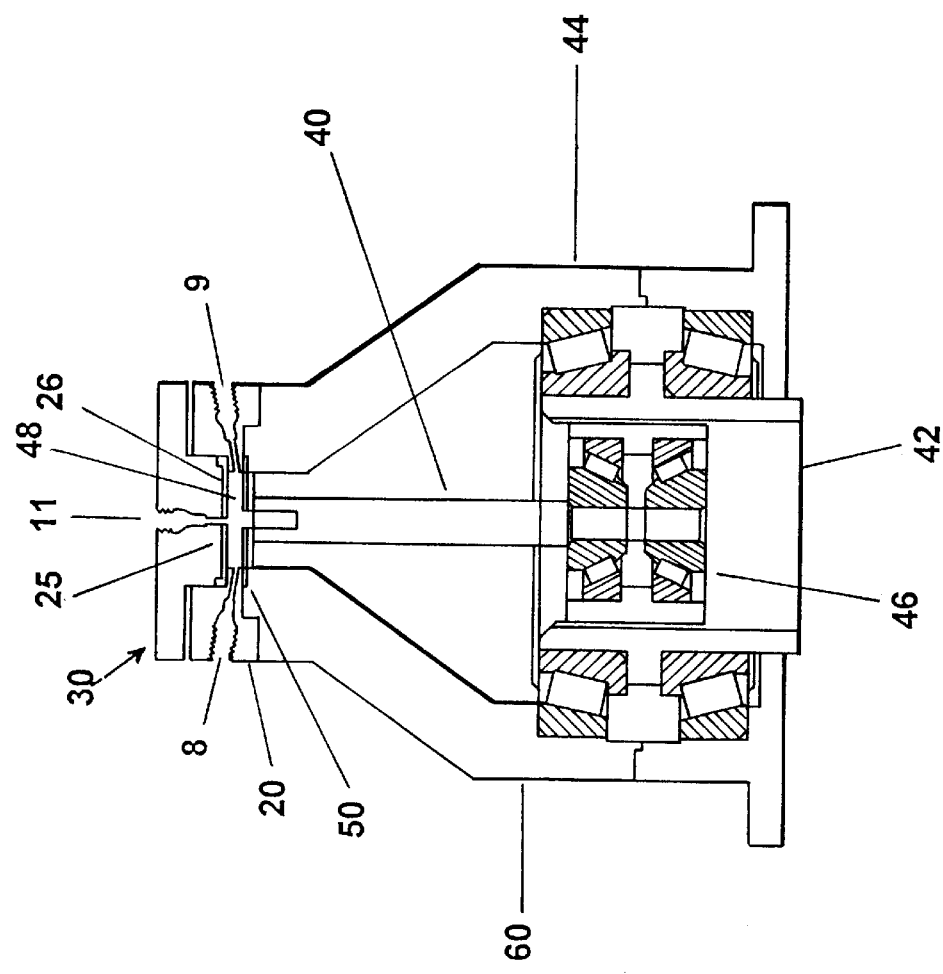
FIG. 3 is a schematic representation of a second embodiment of the molecular diversity screening device.

In yet another embodiment, as shown in FIG. 3, the stirring is accomplished by a wobbling motion of fixed (i.e., non-rotating) shaft 40. A fixed stirring disc 48 is attached to the head of the shaft 40, and is located within the binding chamber 26. A silicon sealing membrane 50 is clamped between the shaft 40 and the disc 48 with the periphery of the sealing membrane 50 sealed against the lower assembly 20 to seal the binding chamber 26 and to keep the shaft and disc from rotating. The bottom of the shaft 40 is mounted to a wobble assembly.

The wobble assembly includes a rotating wobble block 42 mounted in a set of outer pre-loaded bearings 44. The wobble block axis of rotation is concentric with the center of the stirring disc 48. However, inside the wobble block 42 is mounted another set of inner pre-loaded bearings 46 whose axis of rotation is slightly offset from the axis of rotation of the wobble block 42. The bottom of the shaft 40 is mounted to the inner pre-loaded bearings 46 at its axis of rotation. Because the inner bearings and bottom of the shaft is offset, the shaft 40 is aligned about 0.5 degrees from normal. The top face of the stirring disc 48 is then about 0.5 degrees off from the plane of the ultrafiltration membrane 25. The resulting wobbling motion of the disc 48 is the orbiting angular deflection of the disc 48 relative to the membrane 25 caused by rotation of the wobble block 42.

A major advantage of this arrangement is the nature of the resultant fluid motion which reduces protein polarization on the membrane, gives effective mixing, and does so without high shear forces which can be detrimental to maintaining the receptor in its native state. Turning of the wobble block 42 causes the offset bottom of the shaft 10 to orbit around the center of the wobble block's axis of rotation. This wobbling, or orbiting, of the bottom of the shaft is transmitted as an orbiting angular deflection of about 0.5 degrees to the stirring disc 48 in the binding chamber 26. The wobbling motion causes a wave of fluid flow in a circular motion in the binding chamber. In addition, there is a tendency for this pressure wave to cause backward flow through the membrane in the trough of the wave, thus dislodging receptor molecules that might be clogging the membrane pores.

The volumes and shape of the binding and effluent chambers are important to maximize efficiency of the device. The volume of the binding chamber is chosen to provide sufficient receptor or its complex to trap the desired specific compound in sufficient quantity to be detected by the chosen detector or bioassay system. The ability of the device to trap specific compounds depends upon the concentration of the binding receptor, the affinity of the specific compound and the amount of compound in the chemical library. Typically, the concentration of receptor is chosen to be about 100 times the dissociation constant of the specific compounds for the chosen receptor. Thus, if compounds with dissociation constants of $10^{-8}$ molar or greater are desired, the concentration of receptor in the binding chamber would be $10^{-6}$ molar. For a mass spectrometer detector capable of detecting 10 pmoles of specific compound, the chamber volume in this example would need to be 100 µL. For maximum flow rate, which provides a narrow band of elution and increases efficiency of detection, this volume preferably should be distributed over a membrane whose surface area is as large as feasible, yet which will still allow sufficient depth in the binding chamber in which to locate stirring means.

Figure 4:
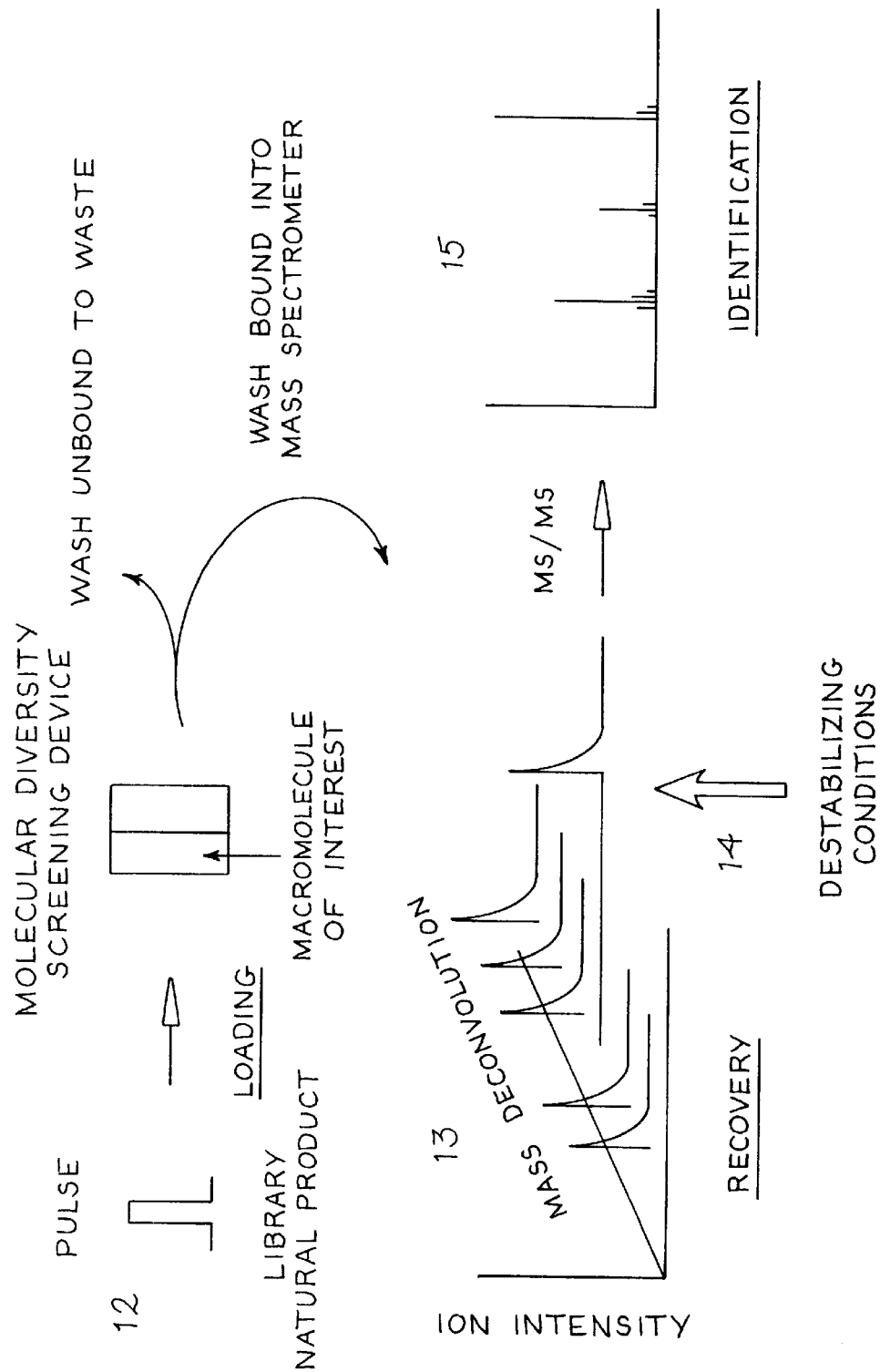
FIG. 4 is a schematic representation of an outcome of a molecular diversity screening method.

The method according to the present invention consists of five steps indicated schematically in FIG. 4 and discussed in detail below: 1) receptor loading and washing, 2) library loading and specific compound binding, 3) washout of non-specific compounds, 4) release and recovery of specific compounds, and 5) analysis of specific compound released.

After loading the target receptor into the binding chamber 26 via the inlet port 8, as depicted in FIG. 2, the molecules to be screened in the form of a chemical library or natural product extract are introduced into the binding chamber via the same port. This is shown as a pulse concentration injection 12 in FIG. 4. Both of these injections are under thermal and buffer conditions favorable to maintaining the receptor in its native active state. As discussed herein, the final concentration of the receptor is chosen based on the desired affinity of the specific compound to be selected. The system is then washed through the effluent port 11 with several chamber volumes of buffer to remove unbound and weakly bound compounds. This can be carried out with the waste valve 4 (FIG. 1) closed for analysis of unbound compounds, as shown as Mass Deconvolution 13 in FIG. 4, or with it open, discarding unbound compounds. At this point, the binding chamber contents are changed in a manner to release bound compounds, as shown as destabilizing conditions 14 in FIG. 4, which are washed into the selected analyzer. In one embodiment this analyzer is a tandem mass spectrometer where the molecules are separated according to mass, subsequently fragmented and the fragments again analyzed according to their mass 15.

A distinguishing feature and a major advantage of the molecular diversity screening method over other methods is that both the receptor molecules and compounds are completely free in solution. In other methods, the receptor is tethered or linked covalently to a solid substrate. It is well understood in the industry that such tethered receptors may not perform as in their native state and are prone to both false positive and false negative results.

The molecular diversity screening device is loaded with a solution containing the macromolecules of interest, e.g. a receptor. Loading is accomplished by injection through the inlet port 8 in FIG. 2 into the binding chamber 26. The binding chamber 26 is then flushed with buffer, such as phosphate, HEPES, or TRIS, solution of a composition chosen to maintain the native structure and activity of the receptor, by introducing the buffer also through the inlet port 8. Effluent from the chamber is led away through the effluent port 11 in FIG. 2.

The device is preferably flushed with two to three chamber volumes of buffer to reduce background signal at the detector and to wash away any low molecular weight impurities present in the macromolecular receptor preparation.

The ultrafiltration membrane 25 shown in FIG. 2 is preferably chosen so as to retain the receptor by size, without binding receptors by, e.g., hydrophobic interaction or other nonspecific interactions. Thus, a molecular-weight cutoff specified for the membrane is preferably well below the molecular weight of the receptor. However, the ultrafiltration membrane should allow free passage of the small molecules of the library to be screened, so that these library compounds are not retained on account of their size. The membrane should be chosen to have as little affinity for the compounds to be assayed as possible (e.g. hydrophilic membrane for hydrophobic compounds), though experiments without receptors present can be used to control for these non-specific interactions.

After the molecular diversity screening device has been loaded with receptor molecules, the chamber is suitably flushed. An aliquot of a solution containing the library of compounds to be screened is introduced by injection through inlet port 8 in FIG. 2. This loading phase may be the injection of a very short pulse of solution containing the library or pool of compounds, or it may involve continued injection of such a solution over an extended period of time.

The device is then flushed with buffer to wash out or elute compounds that are weakly bound or not bound at all to the receptor. At the same time, compounds bound weakly and nonspecifically to parts of the binding chamber or membrane are eluted. This washing phase of the process is an essential element of the process, and serves to separate low-affinity compounds from high-affinity compounds. The removal of weakly and nonspecifically bound compounds will require washing the chamber with several chamber volumes of buffer as defined by Eq. 7. From Eq. 7 a ten-fold reduction in free compound concentration is predicted to require about 2.3 chamber volumes to be flushed through the device. Approximately 7 chamber volumes are needed to reduce the free compound concentration by a factor of 1000, and flushing with about 14 chamber volumes will reduce the free compound concentration by about a factor of $10^6$.

The buffer used for washing the device is preferably made up so as to maintain the native structure and activity of the macromolecular receptor while maintaining the solubility of all the compounds in the library, and while being compatible with all the component parts of the molecular diversity screening device and associated apparatus, including the detector. For example, a volatile buffer such as ammonium acetate might be used for compatibility with mass spectrometric detection. Because the native structure and activity of the receptor are maintained, the receptor will continue to bind compounds in the library. In particular, the receptor molecules will tend to selectively bind and retain those compounds with the highest affinity for the receptor.

The ultrafiltration membrane in the device retains in the binding chamber the macromolecular receptor and any complexes of this receptor with compounds in the library. Thus, compounds that are only weakly bound or not bound at all are separated by elution from those compounds that are retained by the macromolecular receptor, which are those with higher affinity for the receptor. The selection of higher affinity compounds for the receptor molecule is relative and dependent upon the concentration of receptor molecule. Typically, compounds differing by a factor of 10 or greater in their affinity for a given receptor molecule may be separated by these methods.

The device is now flushed with a solution of different composition than the buffer used in the preceding step. This second solution should be made up so as to maintain the full solubility of all the compounds in the library being screened, and to maintain compatibility with all the component parts of the molecular diversity screening device and associated apparatus. However, the constitution of this solution should be chosen to destabilize the receptor-specific-compound complex sufficiently so as to cause the receptor to release its compounds and not rebind them with any appreciable affinity or specificity. This change in buffer composition may include, but is not limited to, changes in Ph, ionic strength, hydrophobicity, temperature, and competing compounds. This stage of the process is referred to as the recovery phase.

By destabilizing the environmental conditions that facilitate binding, all of the molecules in the library of compounds that were being retained by the macromolecular receptor are essentially simultaneously released from the receptor molecules. Because these compounds are now free in solution, they are eluted past the ultrafiltration membrane and out of the effluent chamber as a bolus and may now be recovered from the effluent stream and characterized by chemical, spectral and biological means known to those of skill in the art, and dictated by the type of chemical compounds being assayed.

In an embodiment, the effluent from the molecular diversity screening device 3 (FIG. 1) is directed through a waste valve into a tandem mass spectrometer. In this embodiment, the receptor molecule is loaded into the device and, with the waste valve 4, (FIG. 1) open, flushed with compatible buffer. The library is then introduced and the device washed again with compatible buffer with the waste valve 4, (FIG. 1) open, leaving in the binding chamber 26 (FIG. 2) only those compounds specifically bound to the receptor. With the waste valve closed and the effluent from the device directed into the mass spectrometer, the recovery phase is specifical The specifically bound compounds eluted in the recovery phase are then directed into the spectrometer where they are separated into compounds of different mass and the ion fragments of these different compounds analyzed for structural information.

The molecular diversity screening device can be used to accumulate preferentially high-affinity compounds from a pool or library of many different compounds. The low-affinity compounds can be eluted from the device, leaving behind the high-affinity species as complexes with receptors. After the low-affinity species have been eluted, the buffer or solvent passing through the device can be changed to one that causes the release of the compounds from the macromolecular complex, and they will then be eluted from the device.

Mathematical Models for the Operation of the Present Invention

To provide estimates of the volumes needed to accomplish the washing and recovery of a high-affinity compound, and to provide estimates of the amount of high-affinity compound that may be recovered, mathematical models are developed for solution flow through the molecular diversity screening device and of compound retention by receptor molecules in such a device. A simple model of fluid flow through the molecular diversity screening device is applied first to the volume of solution needed to wash the low-affinity species away. Then the amount of high-affinity compound that may be retained by receptors in the molecular diversity screening device is considered. Finally, the fluid-flow model is again applied to estimate the volume needed to elute the high-affinity species during the recovery phase.

In the treatment of the flow of solution through the molecular diversity screening device any complexation of compound by receptors is ignored, and the focus is on the behavior of a molecular diversity screening device without any added receptor. An assumption is that the binding chamber is uniformly and instantaneously mixed upon entry of a fresh portion of buffer into the device. The flow rate of buffer through the system is assumed to be constant. Starting with a molecular diversity screening device charged with a buffer solution containing a compound at a concentration $C_0$, this corresponds to having $m_0$ moles of compound present in the chamber. The volume of the chamber is taken as $V_c$. The solutions are taken as incompressible, the assumption is that the chamber volume does not change. The solution is so dilute that the excluded volume or partial molar volume corrections due to the presence of the compound are considered negligible. Pure buffer is then pumped through the system, so that the compound is eluted from the device.

In order to pump buffer into the binding chamber an equal volume of solution (containing compound) is removed from the binding chamber. An infinitesimal volume dV of solution is removed from the chamber, in order to make room for an infinitesimally small volume dV of pure buffer. The volumes must be equal since the solutions are incompressible. Removal of the volume dV causes the chamber to lose an infinitesimally small amount of compound, dm, which departs with the solution. The relation is $$dm = C_0 \cdot dV \qquad \text{Eq. (1)}$$

Now an infinitesimally small volume of pure buffer is introduced to bring the volume of solution in the chamber back up to $V_c$. This dilutes the remaining compound in the chamber by an infinitesimally small amount; the change in concentration is given by $$-dC = \frac{dm}{V_c} = \frac{C_0 dV}{V_c} \qquad \text{Eq. (2)}$$

(The negative sign accounts for the removal of compound from the chamber and the dilution of the compound remaining in the chamber.)

The process of removal of a portion of the device's contents, and its replacement with pure buffer is assumed to occur repeatedly. The compound concentration in the binding chamber will steadily decline as compound is removed; a continual dilution of compound is predicted in the chamber. In fact, at any time t, when the compound concentration in the chamber is C(t), $$-dC = \frac{dm}{V_c} = \frac{C(t) dV}{V_c} \qquad \text{Eq. (3)}$$

From this the rate of change of concentration with time, which describes the rate of elution of compound from the chamber, is determined to be:

$$-\frac{dC}{dt} = \frac{C(t)}{V_c} \frac{dV}{dt} \qquad \text{Eq. (4)}$$

which can be rewritten as $$-\frac{dC}{dt} = \frac{C(t)}{V_c} \dot{V} = k_2 C(t) \qquad \text{Eq. (5)}$$

where the rate of flow of buffer, dV/dt, is represented as $\dot{V}$. Thus the rate parameter $k_2$ used previously (Chen, 1993) is identified as the ratio of the flow rate to the chamber volume:

$$k_2 = \frac{\dot{V}}{V_c} \qquad \text{Eq. (6)}$$

Eq. 5 may be integrated to give the basic equation describing the compound elution:

$$C(t) = C_0 e^{-\dot{V}c} = C_0 e^{-k_2 t} \qquad \text{Eq. (7)}$$

or $$\frac{t\dot{V}}{V_c} = \frac{V(t)}{V_c} = -\ln\left(\frac{C(t)}{C_0}\right) \qquad \text{Eq. (8)}$$

where C(t) is the free compound concentration at time t, $C_0$ is the original concentration of compound, $\dot{V}$ is the flow rate of buffer through the apparatus, V(t) is the volume eluted from the chamber at time t, and $V_c$ is the volume of the chamber.

From Eq. 7 or 8, a ten-fold reduction in free compound concentration is predicted to require about 2.3 chamber volumes to be flushed through the device. Approximately 7 chamber volumes are needed to reduce the free compound concentration by a factor of 1000, and flushing with about 14 chamber volumes will reduce the free compound concentration by about a factor of $10^6$. See Example 2.

A simple mathematical model for the amount or quantity of high-affinity compound that may be retained by a receptor in the molecular diversity screening device is considered. This treatment will also permit estimation of the amount of high-affinity compound that may be accumulated from a dilute solution of that compound being passed through a molecular diversity screening device that contains a solution of a specified receptor. The following definitions are used:

- $[L_i]$ is the concentration of the i-th compound in the pool or library of compounds;
- $[L_i]_T$ is the total concentration of the i-th compound, both free in solution and in complex;
- $[L_i]_F$ is the concentration of the i-th compound free in solution;
- $[M]_T$ is the total concentration of the receptors in the chamber;
- $[ML_i]$ is the concentration of receptors with the i-th compound bound;
- $[M]_F$ is the concentration of receptors with no compounds bound;
- $Y_i$ is the degree of binding saturation of the receptor with the i-th compound, a quantity defined as the ratio of the moles of receptor binding sites occupied by the i-th compound, to the total number of moles of receptor binding sites present and capable of binding the i-th compound;
- $K_i$ is the binding or association constant for binding of the i-th compound with the receptor.

The following assumptions are made:

- There are m different species of compounds in the pool or library;
- The receptor has only one binding site;
- The compounds in the pool or library must compete for binding to this single site;
- The binding chamber is charged with a solution containing macromolecular receptor and the pool of compounds, at equilibrium.

The binding equilibrium for the i-th compound is $$L_i + M \rightleftharpoons ML_i \qquad \text{Eq. (9)}$$

with the equilibrium constant $$K_i = \frac{[ML_i]}{[L_i]_F[M]_F} \qquad \text{Eq. (10)}$$

The concentration of the species $ML_i$ is given by $$[ML_i] = Y_i [M]_T \qquad \text{Eq. (11)}$$

By conservation of mass it follows that $$[M]_F = [M]_T - [ML_1] - [ML_2] - [ML_3] - \ldots - [ML_m] \qquad \text{Eq. (12)}$$

or using the dummy index j in place of i to identify receptor-compound complexes, $$[M]_F = [M]_T - \sum_{j=1}^{m} [ML_j] \qquad \text{Eq. (13)}$$

Using Eq. 10, this becomes $$[M]_F = [M]_T \left(1 - \sum_{j=1}^{m} Y_j\right) \qquad \text{Eq. (14)}$$

Now substitution of Eq. 11 and Eq. 14 into Eq. 10 gives $$K_i = \frac{Y_i [M]_T}{[L_i]_F \left(1 - \sum_{j=1}^{m} Y_j\right)[M]_T} \qquad \text{Eq. (15)}$$

This last equation yields a relation for the free compound concentration in terms of the binding constant $K_i$ and the degrees of saturation $Y_1, Y_2, \ldots, Y_m$:

$$[L_i]_F = \left(\frac{Y_i}{1 - \sum_{j=1}^{m} Y_j}\right) \cdot \frac{1}{K_i} \qquad \text{Eq. (16)}$$

$$[L_i]_{incoming} < \left(\frac{Y_i}{1 - \sum_{j=1}^{m} Y_j}\right) \cdot \frac{1}{K_i} \qquad \text{Eq. (17)}$$

(the subscript "incoming" indicates that the compounds are flowing into the binding chamber) then dissociation and loss of complexes occurs. The overall concentration of compound i in the chamber will decline.

If, however, $$[L_i]_{incoming} > \left(\frac{Y_i}{1 - \sum_{j=1}^{m} Y_j}\right) \cdot \frac{1}{K_i} \qquad \text{Eq. (18)}$$

then more complexes are formed.

At equilibrium, the total concentration of compound i in the binding chamber at any moment is given by the amount free in solution plus the amount in complex with receptor:

$$\begin{aligned}[L_i]_T &= [L_i]_F + [ML_i] \\ &= \left(\frac{Y_i}{1 - \sum_{j=1}^{m} Y_j}\right) \cdot \frac{1}{K_i} + Y_i [M]_T \end{aligned} \qquad \text{Eq. (19)}$$

If the situation is considered where the binding chamber is initially loaded with receptor but the pool of compounds to be screened is not yet injected into the system, no compounds from the pool are present initially in the chamber and the initial free compound concentrations in the chamber are of course zero. Now a continuous stream of compounds is introduced into the device so that the free concentration of each compound rises in the chamber. This is the "loading" phase of operations, described herein. The compounds compete for binding to the sites on the receptors. When the loading phase is continued over an extended period of time, a steady-state of binding and dissociation is reached, such that the material eluted from the chamber contains compounds at concentrations equal to the respective free compound concentration in the chamber at that moment. This relationship is expressed as $$[L_i]_{outgoing} = [L_i]_F \qquad \text{Eq. (20)}$$

where the subscript "outgoing" indicates that this material or compound has passed through the ultrafiltration membrane and is moving toward the detector.

$$[L_i]_T = \left( \frac{Y_i}{1 - \sum_{j=1}^{m} Y_j} \right) \cdot \frac{1}{K_i} + Y_i[M]_T \qquad \text{Eq. (21)}$$

The relation of Equation 21 must hold inside the binding chamber for all species of compound, simultaneously, during the steady state of injection and elution of the compound pool. The numerical value of any particular $Y_i$ in the steady state is set not only by the corresponding binding constant $K_i$ but also by the competition among all the other compounds present, as reflected in the dependence of $[L_i]_T$ on all of the $Y_j$. Of course, compounds with higher affinity for the macromolecular receptor will have numerically larger values of $Y_i$ than those compounds whose affinity is lower.

For example, a high-affinity compound with $K_i$ equal to $10^9$ molar$^{-1}$ requires a free compound concentration of only about $10^{-8}$ molar to keep the binding saturation $Y_i$ above 0.95 (the receptor being 95% saturated with this compound). By comparison, a low-affinity compound with $K_i$ equal to $10^6$ molar$^{-1}$ requires a free compound concentration of about $10^{-5}$ molar to keep its binding saturation $Y_i$ above 0.95. In each case, for simplicity it is assumed that there are no competing species; competitors will reduce the respective degrees of binding saturation, and the calculation is long and involved and does not affect the main concepts of the invention.

Suppose that the compounds were loaded into the binding chamber at a concentration of $10^{-4}$ molar, a not-unreasonable concentration of an individual species in a compound library solution. In the absence of competitors, the high-affinity compound will maintain $Y_i$ above 0.95 until the washing phase reduces the free compound concentration in the chamber to below $10^{-8}$ molar. This corresponds to washing the chamber so as to dilute the compound by a factor of $10^4$, and under typical operating conditions, this will require washing the chamber with many chamber-volumes of buffer.

The situation is quite different for a compound of low binding affinity. Even in the absence of competitors, the low-affinity compound will maintain $Y_i$ above 0.95 only until the washing phase reduces the free compound concentration in the chamber to below $10^{-5}$ molar. This is only a ten-fold dilution of the free compound concentration for this weak-binding compound. This level of dilution will occur with washing of the device with only a few chamber volumes.

In other words, after just a few chamber volumes of washing, the low-affinity compounds will experience very substantial drops in $Y_i$, and the $Y_i$ for such compounds will quickly approach negligible values. Conversely, the $Y_i$ for high-affinity compounds will not decline until much more washing of the chamber has occurred. Certainly, in terms of absolute numbers of moles, much of the high-affinity compound will have been washed from the chamber when virtually all of the low-affinity compound has been washed away. The point is, the receptor will still be nearly saturated with the high-affinity species after this washing away of the low-affinity species.

Washing of the device is halted before substantially reducing the degree of binding saturation for the high-affinity compound(s). At this point, there is a separation of high-affinity compound(s) from all compounds of lower affinity; the high-affinity compound(s) will be retained in complexes with the receptor and the lower affinity compounds have been eluted from the chamber. Subsequently the high-affinity compound(s) may be released from the receptor by replacing the buffer with a solvent designed to cause release of the compound(s) from the receptor. This solvent might destabilize the receptor's conformation, or provide a better solvation of the compound(s), or some combination of the two effects, but the net effect is to cause dissociation of the complex.

After release of the high-affinity compound(s) from the receptor, the compound(s) can be washed from the chamber. The effluent from the chamber is now analyzed to discover which members of the compound library have been retained by the receptor; this identifies the high-affinity compound(s). See Example 5.

If two or more members of the library have equal high affinities for the receptor, these species will be retained by the receptor in a way very similar to that described above for retention of a single high-affinity species. However, when there are two high-affinity species present, they will compete for binding to the receptor. If they are each initially present in equimolar amounts, the degree of binding saturation for each will equal just half that expected if either one were present alone. The reduction in degree of binding saturation is due to competition. If three such compounds are present, then the degree of binding saturation will be reduced to one-third the value expected when only a single high-affinity compound is being complexed with the receptor. In general, for N such compounds, we will have an N-fold reduction in the degree of binding saturation for each compound due to this competition.

The molecular diversity screening device may be used to accumulate from a dilute solution a compound with high affinity for a receptor. A minimal requirement for accumulation of compound to reach a degree of binding saturation $Y_i$ for, say, the i-th compound, is that the concentration of compound entering the chamber be greater than the equilibrium concentration of free compound needed to support that degree of saturation:

$$[L_i]_{incoming} > \left( \frac{Y_i}{1 - \sum_{j=1}^{m} Y_j} \right) \cdot \frac{1}{K_i} \qquad \text{Eq. (22)}$$

Under these conditions the compound forms complexes with the receptor and increases the degree of saturation $Y_i$ of the receptor with this species. So long as the inequality holds for an incoming stream of compound i, the concentration of complexes in the chamber will rise and so will the quantity $Y_i$.

Accumulation of compound will continue until either the receptor is saturated with the compound and no more compound may be retained by complexation, or a lesser degree of saturation $Y_i$ is reached such that the concentration of compound entering the chamber now satisfies the equality:

$$[L_i]_{incoming} = \left( \frac{Y_i}{1 - \sum_{j=1}^{m} Y_j} \right) \cdot \frac{1}{K_i} \qquad \text{Eq. (23)}$$

This relation takes account of competition from other compounds for binding to the receptor. When there are no competing compounds and only the single species of high-affinity compound is present in the incoming stream of solution, then the relation simplifies to $$[L_i]_{incoming} = \left( \frac{Y_i}{1 - Y_i} \right) \cdot \frac{1}{K_i} \qquad \text{Eq. (24)}$$

It is important to notice that for high-affinity compounds, the incoming compound solution may be quite dilute and still satisfy the inequality of Eq. 22. For example, in the absence of any binding competition, a compound whose binding constant for the receptor is $10^9$ molar$^{-1}$ may be accumulated to a degree of saturation of the receptor of 90% ($Y_i$=0.90), so long as the concentration of the compound in the incoming solution is greater than $9 \times 10^{-9}$ molar (nine times the dissociation constant here). Thus a concentration of compound in the incoming solution that is about ten times the dissociation constant for the receptor-compound complex should suffice for accumulation of the compound to a degree near saturation of the receptor. If the receptor were present at micromolar concentrations, then micromolar concentrations of high affinity compound may be accumulated (as complexes with the receptor) from a solution where the compound concentration is at $10^{-8}$ molar, one hundred-fold more dilute.

Only a rather small volume of destabilizing solvent need be passed through the molecular diversity screening device to release and elute a substantial fraction of the high-affinity compound retained by the receptor, provided that the destabilizing agent can be made up at sufficiently high concentration. Mathematical analysis of the behavior of the binding chamber (similar to the previous description of the washing of the chamber to remove compounds of low binding affinity) leads to the following equation that describes the rise in concentration in the chamber of the destabilizing agent:

$$C(t) = C_0(1 - e^{-Vt/V_c}) \qquad \text{Eq. (25)}$$

or $$\frac{V(t)}{V_c} = \ln\left( \frac{C_0}{C_0 - C(t)} \right) \qquad \text{Eq. (26)}$$

where $C_0$ is the concentration of the agent as injected into the apparatus and $C(t)$ is its concentration in the chamber at time t; other symbols are as defined before. These equations predict that it requires only about 3 chamber volumes to bring the concentration of the destabilizing agent in the chamber up to 95% of $C_0$, and with only about one chamber volume of the new solution, the concentration of the destabilizing agent in the chamber will rise to about 63% the value of $C_0$. For example, using a solution for injection of 95% methanol (v/v) to destabilize the receptor-compound complex, pumping one chamber volume of this solution through the apparatus will bring the methanol concentration in the chamber up to about 60% methanol, a concentration that denatures many proteins and which should release any specifically-bound compounds. Passage of two chamber volumes through the chamber would bring the methanol concentration in the chamber up to 82% methanol. Thus it is possible to increase the concentration of destabilizing agent within the chamber to rather high levels, with passage of only one or two chamber volumes.

Also, the mathematical model predicts that if the compound were entirely released at a certain concentration of destabilizing agent, so that the compound were now to be eluted from the chamber in an exponential decay, it would require only one chamber volume to remove about 63% of the compound from the chamber, once the destabilizing agent reaches that certain concentration effecting release of the compound. After elution of one chamber volume the free compound concentration remaining in the chamber would be reduced to approximately 37% of its value at the time of release. Passage of two chamber volumes would elute approximately 86% of the compound and leave only about 14% in the chamber.

If the assumption is that passage of one chamber volume of destabilizing agent were to bring the concentration of this agent up to a level sufficient to release all of the compound from complexation with the receptor, then passage of a total of two chamber volumes of destabilizing solution through the chamber should elute approximately 63% of the compound. If a further assumption is that the receptor concentration were at $10^{-8}$ molar in the chamber, and that the receptor were 95% saturated with compound at the point where the destabilizing agent is introduced, then the model predicts a free compound concentration of $0.95 \times 10^{-8}$ molar in the chamber after passage of the first chamber volume of the destabilizing agent solution. Passage of the second chamber volume of the destabilizing agent solution through the chamber reduces the free compound concentration in the chamber to 37% of this initial value, or to about $0.35 \times 10^{-8}$ molar in the chamber. The concentration of compound in the effluent from the chamber starts at whatever the concentration was before introduction of the destabilizing agent solution, then rises quickly to a value somewhat less than $0.95 \times 10^{-8}$ molar, and then declines. See Example 5. However, in this experiment the binding chamber is unstirred and is unlikely to directly represent this theoretical interpretation (times are expected to be longer than the theoretical prediction). Consequently stirring is optional, but preferred, given the longer analysis times for the non-stirred situation and its tendency to reduce the ability of the system to separate compounds of different affinities.

If the receptor concentration were higher, the concentration of eluted compound would be higher. Receptor concentrations in the micromolar range are reasonable and typical. In such a case where the receptor concentration is at one micromolar, at 95% saturation of the receptor with compound, the eluted compound concentration would rise to about $0.95 \times 10^{-6}$ molar and then decline.

The absolute numbers of moles of compound retained and then eluted in this fashion will depend on the chamber volume. Larger chamber volumes will allow one to retain larger numbers of moles of compound to be retained. As discussed herein, chamber volumes and thus moles of compound retained, are adjusted to match the sensitivity of the chemical, spectral or biological assay being employed. The chamber volumes are measured by determining the $k_2$ value as previously described (Chen, 1993) and application of Eq. 6 knowing the flow rate at which $k_2$ is determined. See Example 1.

Many different types of compound libraries may be screened by the molecular diversity screening system. Among these types of libraries are those derived from various polymers such as peptides, oligonucleotides, phosphorothioate oligonucleotides, oligo- and polysaccharides, peptidomimetics, and "peptide" nucleic acids or PNAs. In addition, chemical libraries of nonpolymeric small organic molecules using solid phase synthesis can be tested after release from the polymer. Importantly, the invention can also be applied to small organics produced free in solution as described in Example 5. Further, molecular diversity from plant or marine sources may be screened by the invention.

The compounds in the library to be screened must be readily soluble in the buffer used to elute the molecular diversity screening device during the washing phase. They must also be soluble in the solution used to perturb the macromolecular receptor during the recovery phase. Compounds with little or no solubility in the buffer used during the washing phase will precipitate in the binding chamber and foul the chamber and membrane. Similarly, compounds with little or no solubility in the solution used to perturb the receptor will also tend to precipitate and foul the chamber and/or membrane.

The compounds must be chemically stable in both the washing buffer and in the recovery solution, at least over the time period of the entire process, from injection into the device to elution during the recovery phase. Appreciable degradation or reaction of the compounds over this time might interfere with their specific retention by the receptor, it would also complicate their identification after they are recovered from the molecular diversity screening device. Furthermore, the compounds should be unreactive toward component parts of the device, and the compounds should be unreactive toward other members of the library being screened, for these same reasons.

In general, the amount of receptor necessary to detect a specific compound should match the sensitivity level of the detector. For mass spectrometry as the detection device, as little as 100 femtomole of receptor could provide structural information on high affinity compounds in a library. The amount of a specific compound that can be detected by the invention depends upon the detector sensitivity, amount of receptor, receptor concentration, affinity constant, number of competing compounds and their concentration. For example, using mass spectrometry, a library containing 100 femtomoles of a specific compound with an affinity constant of $10^9$ molar$^{-1}$ in a liter of solution could be detected with a 100 $\mu$L chamber containing a $10^{-7}$ molar concentration of receptor.

Many different types of receptors may be used as binding targets with the molecular diversity screening device. They should, however, obey certain general principles. First, they must be retained by the membrane and not pass through it. Second, they must be stable enough to retain binding activity in the molecular diversity screening device over the time course of the binding assay. Within these two constraints there are many classes of suitable receptors.

A first major class of binding receptors are the many different types of soluble enzymes that are currently targets (or under study as potential targets) for therapeutic intervention. These include proteases (e.g., the HIV protease, elastase, angiotensin converting enzyme, renin, factor $X_a$), nucleic acid polymerases or nucleases (e.g., RNA polymerase of *Escherichia coli*, telomerase, or the reverse transcriptase of HIV), kinases (protein kinase A, protein kinase C, kinases for nucleic acids, and others), and many other enzymes (e.g., ribonucleases, adenosine deaminase, ornithine decarboxylase, HMG-CoA reductase, enzymes involved in prostaglandin synthesis, phosphatases, and phosphorylases). See Examples 4,5,6,7, and 9.

A second major class of binding receptors that would be appropriate for study with the molecular diversity screening system would be other soluble proteins that are targets (or potential targets) for therapeutic intervention. See Example 8. These include structural or contractile proteins (e.g., tubulin, myosin, and others). Peptide and protein hormones would also be suitable in many cases. Another subclass of suitable targets are carrier or storage proteins (e.g., myoglobin, hemoglobin, serum albumin, retinol binding protein and others). See Example 2. Another subclass would be proteins of the immune system or stable fragments of these proteins. Examples here include immunoglobulins, proteins of the major histocompatibility complex [MHC], T-cell receptors, and others. Included here are stable polypeptide fragments of the various proteins as potential binding receptors, since much useful work on binding affinity and specificity has been carried out using only particular segments or fragments of such proteins. Examples include the use of $F_c$ domains of immunoglobulins in the study of antigen binding by antibodies, and the explication of binding and enzymatic activity of the DNA polymerase I of *Escherichia coli* using the so-called Klenow fragment.

A third major class of binding receptors are the nucleic acids (DNA, mRNA, tRNA, and others), and synthetic or man-made analogs of nucleic acids. Man-made analogs include unusual or unnatural replacements of the nucleic acid phosphate diester backbone (e.g., phosphorothioate or phosphonate derivatives), along with the so-called peptide nucleic acids. Other analogs include unusual or unnatural base substitutions (e.g., hypoxanthine replacing guanine or adenine, or 5-fluorouracil replacing uracil, and others), and unusual or unnatural sugar substitutions.

A fourth important class of receptors that can be investigated by the molecular diversity screening system would include membrane-bound receptor proteins (e.g., estrogen receptors, dopamine receptors, benzodiazepine receptors, histamine receptors, enkephelin/endorphin receptors, and insulin receptor), provided that these may be stabilized by appropriate cosolvents, lipids, or detergents, as in lipid bilayer vesicles or liposomes. It may also be possible to employ microsomes as targets for binding and library screening, in the molecular diversity screening device.

There are many other potential types of receptors that could be employed in the molecular diversity screening system to screen libraries of compounds. The method could be used, for example, with polypeptides (both synthetic and natural), polysaccharides (e.g., heparin, hyaluronic acid, polygalacturonic acid, carboxymethylcellulose, and others), and man-made polymers such as polyacrylic acid, to select for or against compounds in the library for desired characteristics of drug release and/or adsorption by these polymers.

Further, the invention may be employed in an embodiment where multiple receptor molecules are examined to determine which binds a particular specific compound. In this embodiment, various receptor molecules are serially examined to define whether a particular compound has affinity. Examples include nuclear receptor proteins, plasma binding proteins, membrane-bound receptors, and may extend to the use of whole cells, microsomes, membrane fragments, tissue homogenates and fractions thereof.

In addition, the invention may be employed in an embodiment where sample multiplexing is applied in greater than two dimensions. Multiplexing in its most general form has been around for many years. (Evans, 1989). Also applied to screening, it involves pooling samples in an X,Y matrix so that the number of assays necessary to identify an active species is only 2√n, where n is the total number of samples to be assayed. (Smith, et al., 1994; Pirrung, 1995). However, for large numbers of compounds the numbers of assays remains large. In the present invention the sample matrix may be extended to the third dimension, greatly reducing the number of required assays.

Consider a Cartesian coordinate system of boxes which are filled with n compounds in a fashion such that no two compounds having identical masses are placed in the same row in the mass direction. See FIG. 5. Summing the compounds along the mass axis (solid arrow) fills each of the X,Y boxes in the front of this matrix with compounds of different masses. Summing the compounds in these front boxes along both the X and Y directions (solid arrows crossing each other) then gives pools $P_x$ and $P_y$.

Application of the invention can identify, i.e. provide a particular Cartesian coordinate of X,Y and mass, for the compound showing binding to the selected receptor in the screening device. Thus, the set of samples is assessed for the presence of high-affinity compounds by assaying the $P_x$ and $P_y$ pools and looking for those masses that show binding at a specific X, Y coordinate.

If the compounds being tested were evenly distributed across a mass range of 200 to 800 amu, then formed or packed into a three-dimensional array with a square face, then the dimensions of this face are l×l, where $l=(n/600)^{1/2}$. The number of assays required to assay this set of samples would be just 2 l. Thus, a set of 15,000 samples could be analyzed in just 10 assays, i.e. 5×5×600 is the volume of the analytical space, and the quantity l here is just 5.

There are problems with indexing when multiple "hits" are present. Such indexing alone may not provide a unique solution, however, with the present invention this can readily be resolved by MS/MS experiments. Thus, in those cases where multiple "hits" are present it is likely that they will be resolved when the molecule's fragmentation pattern is determined in the second mass analyzer of the tandem mass spectrometer.

The following examples are offered by way of illustration, and are not in any way limiting. Those skilled in the art will recognize that different chemical libraries and other sources of molecular diversity may be employed. The size of the molecular diversity screening device, buffer, flow rates and concentrations of reagents may to some extent be varied.

EXAMPLE 1

Molecular Diversity Screening Device Elution Characteristics

Figure 5:
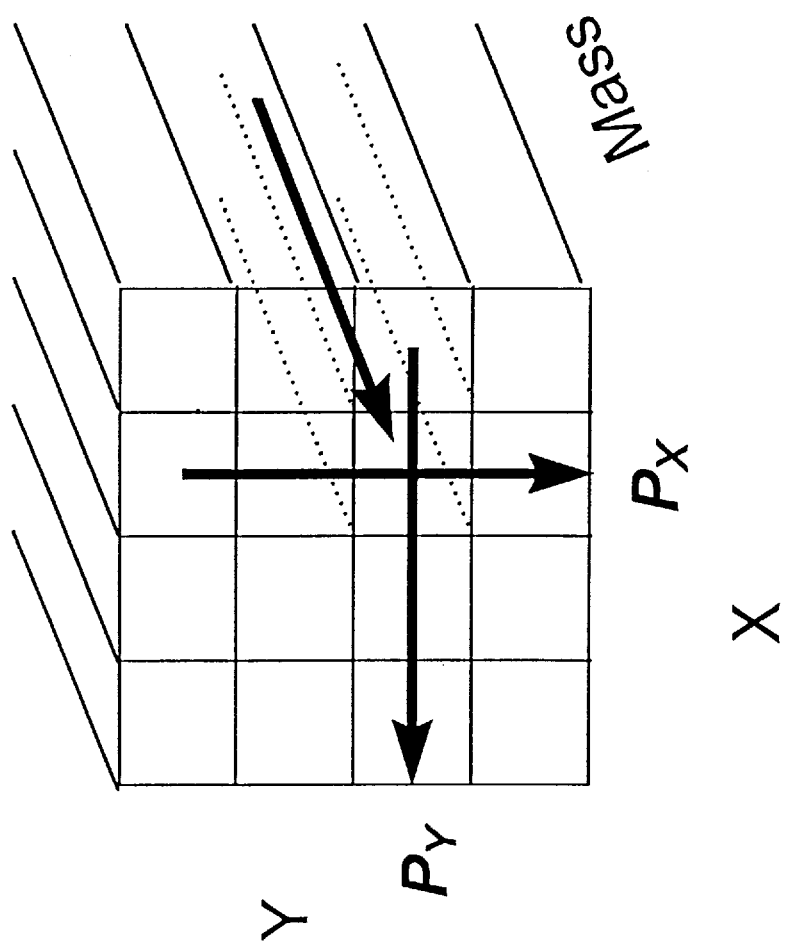
FIG. 5 is a three dimensional schematic representation of sample indexing (multiplexing).
Figure 6:
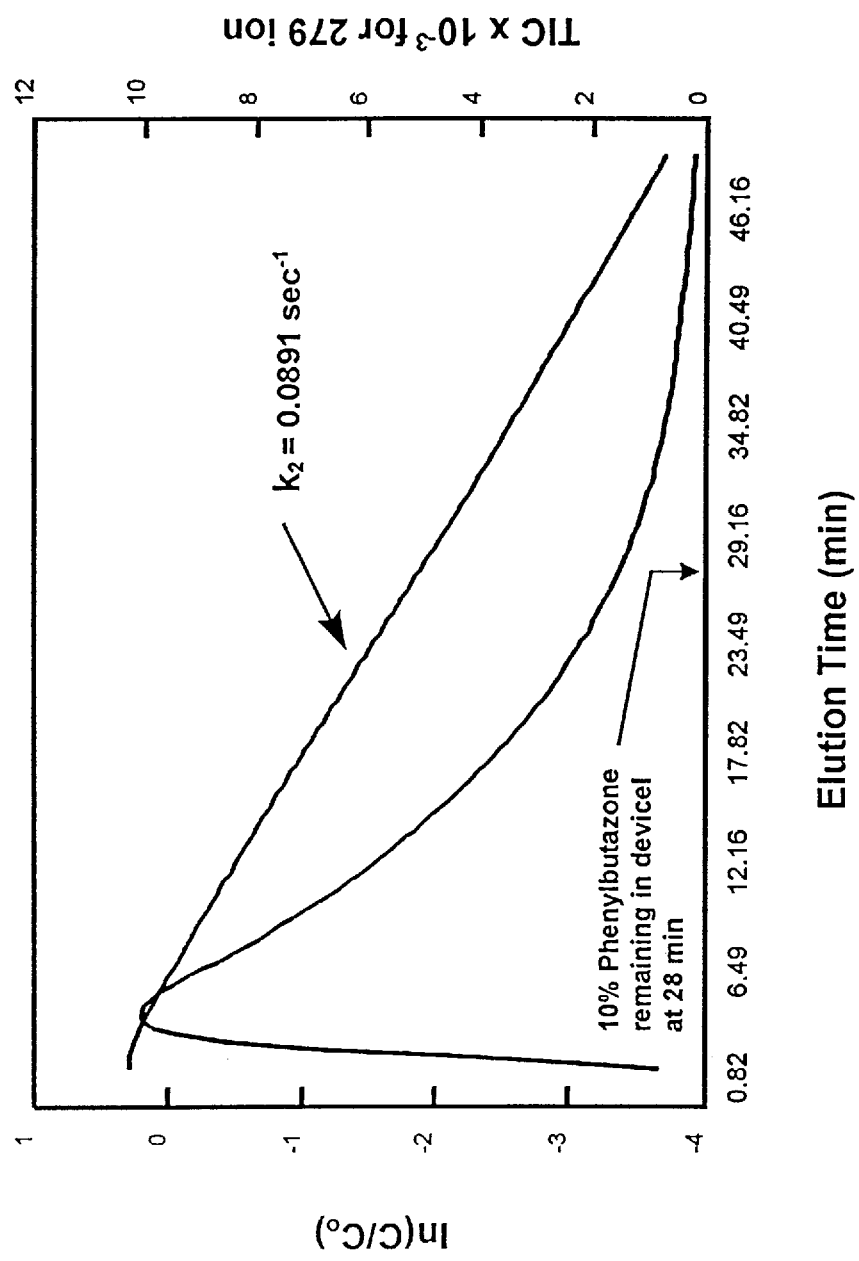
FIG. 6 is a graphical representation of elution-characteristics of the device of FIG. 2 or 3.

Phenylbutazone (12.5 μL×7.3 Mm) was injected into a stirred molecular diversity screening device continuously eluted with water at a flow rate of 100 μL/min. By one method, the volume of this device was determined by measuring the time required to fill the chamber at a constant flow rate and was found to be 1.13±0.02 Ml by this method. The effluent from the device was directed to an electrospray mass spectrometer and the phenylbutazone CID fragment ion at 279 amu was monitored (FIG. 6). As may be seen, the phenylbutazone rapidly rises to a maximum and decays over a period of about 46 min in this device. A plot of $\ln(C(t)/C_0)$ versus time should be linear with a $k_2$ constant equal to the slope. (Chen, 1993) As shown in FIG. 5, the value of $k_2$ is calculated to be 0.0891 sec$^{-1}$. Using this value of $k_2$ in Eq. 6 the chamber volume is predicted to be 1.116 mL, in close agreement with the above volume of 1.13 mL measured in the conventional manner described herein. Important to the use of this type of device to screening molecular diversity is an understanding of the elution curves for various compounds. Eq. 7 predicts that an unretained compound should be reduced in concentration by 90% at a point where after its injection 2.3 chamber volumes have passed through the device. In this experiment, 2.3 times the chamber volume of 1.12 mL divided by the flow rate of 100 μL/min gives a value of 26 min, at which time 90% of the contents of the chamber should be emptied. This is an approximation, because time is required for the phenylbutazone to enter the chamber (ca. 0.8 min) and begin its exponential decay (ca. 1 min). Nevertheless, the calculated value of 26 min is in close agreement with the experimental value of 28 min calculated by integrating the area under the curve in FIG. 6 (arrow indicating 10% remaining in chamber).

EXAMPLE 2

Extraction of Pentachlorophenol by Bovine Serum Albumin

The most abundant serum protein, serum albumin functions as an important blood carrier molecule for many drugs. Competition for sites on the molecule and displacement of one bound drug by another may result in significant drug-drug interactions and potential toxicity or other therapeutic problems. An application of the molecular diversity screening system is to screen for compounds which bind with high affinity to serum albumin. When carrying out any screening assay, the receptor (in this case albumin) when placed in the molecular diversity screening device in the proper concentration extracts any compounds which bind the albumin from a given solution of an library of compounds injected into the device.

In order to demonstrate how a compound may be extracted from solution and bound to a receptor in the chamber, serum albumin (i.e., human serum albumin, bovine serum albumin, and the like) is injected into the molecular diversity screening device (equipped with a 10,000 molecular weight cutoff ultrafiltration membrane) to reach a concentration of approximately 1 μM. The receptor concentration is chosen to be about 100 times the smallest dissociation constant being sought. For albumin-pentachlorophenol, the dissociation constant is approximately $10^{-8}$M. In this experiment, the chamber has a volume of 100 μL and is not stirred, which means that the washout times is longer, but does not prohibit use of such a device for screening. The binding chamber is then washed with binding buffer (i.e., 100 Mm ammonium acetate at Ph 7.4) at 100 μL/min to wash out any low molecular weight impurities. The compound, in this case pentachlorophenol (equimolar or less with respect to the serum albumin in the binding chamber) is then injected into the binding chamber, and elution of pentachlorophenol is monitored using an appropriate detector such as UV absorbance or an electrospray mass spectrometer. An example of the extraction of pentachlorophenol from a binding buffer by bovine serum albumin is shown in FIG. 7 using electrospray mass spectrometric detection.

Figure 7:
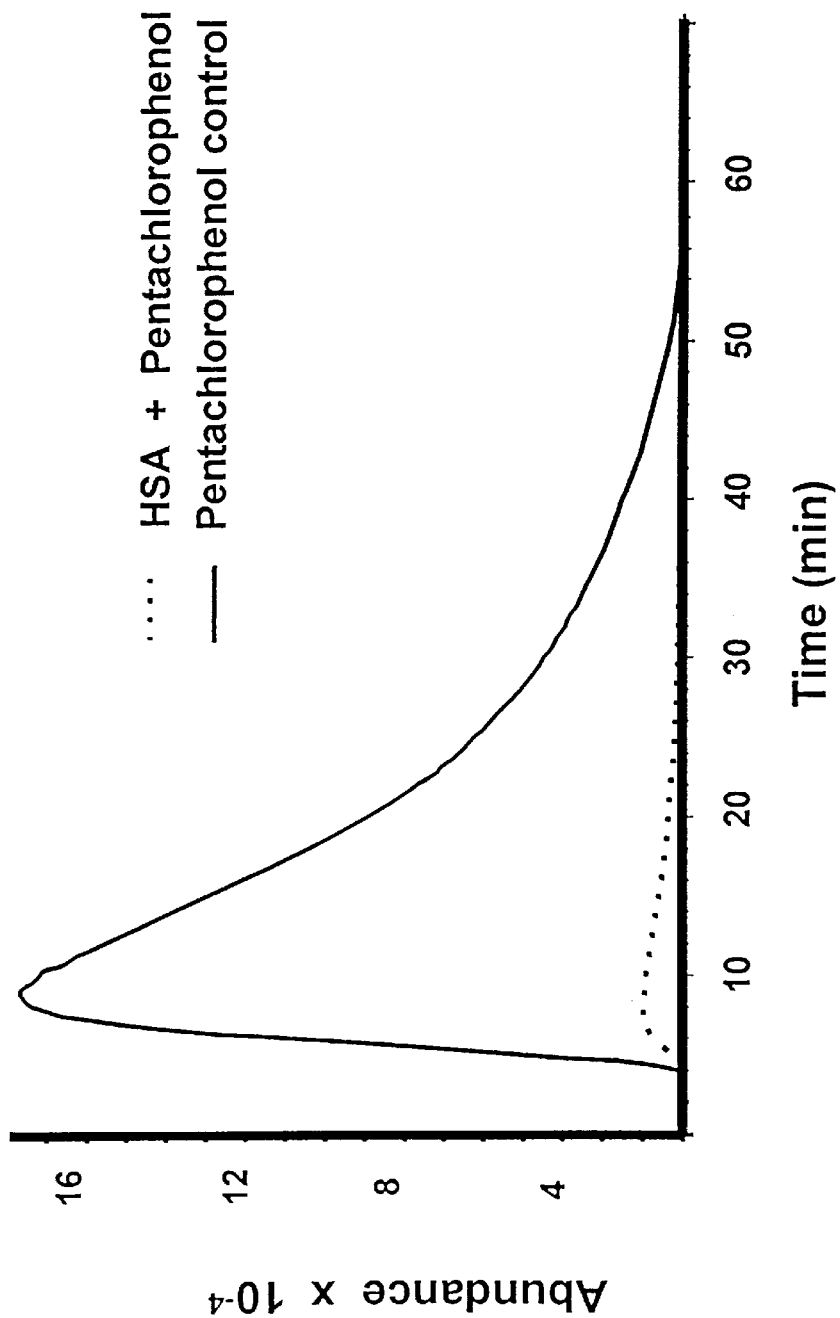
FIG. 7 is a graphical representation of the HSA extraction of pentachlorophenol.

When pentachlorophenol is injected into the binding chamber without serum albumin present, an abundant peak is detected by the mass spectrometer as pentachlorophenol flows through the device unimpeded (FIG. 7, solid curve). After bovine serum albumin is loaded into the binding chamber, another aliquot of pentachlorophenol is injected, but in this case only a trace of pentachlorophenol is detected by the mass spectrometer (FIG. 7, dashed curve) since this compound has been almost completely extracted from the solution by the albumin receptor molecule. Retention of pentachlorophenol in the binding chamber corresponds to tight binding to serum albumin under the predicted concentrations.

EXAMPLE 3

Binding and Release of EHNA from Adenosine Deaminase

Figure 8:
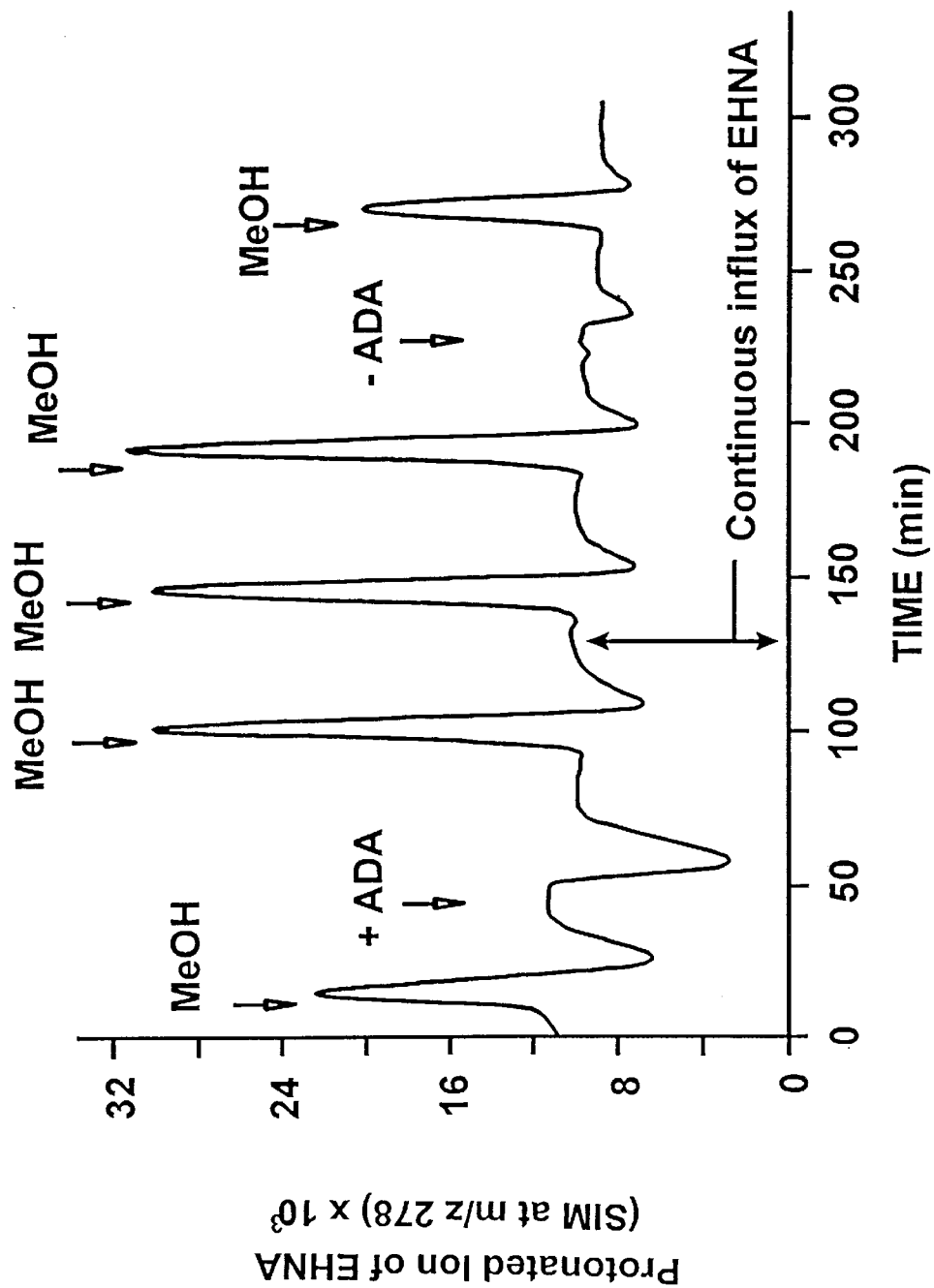
FIG. 8 is a mass spectrometric profile of the binding and release of EHNA from ADA.

A continuous stream of the known adenosine deaminase (ADA) inhibitor, EHNA (erythro-9-(2-hydroxy-3-nonyl)

adenine, with a dissociation constant of $7 \times 10^{-9}$ molar (North, et al., 1979), was introduced at a concentration of $2 \times 10^{-8}$ M (ammonium acetate buffer, 33 Mm) into the molecular diversity screening device. The device effluent was monitored using a mass spectrometer equipped with an electrospray interface run in the single ion monitoring mode at m/z 278. As may be seen in FIG. 8, an ion current due to the EHNA at m/z 278 is seen as a background of about 10,000 marked "Continuous influx of EHNA". At about 10 min, 25 µL of MeOH is injected into the binding chamber resulting in an increase in EHNA—the first peak on the left. This signal is due to an enhanced sensitivity of the detector to EHNA in the presence of MeOH and/or due to release of non-specifically bound EHNA from the device and its parts. At about 40 min, the receptor ADA, in 33 mM ammonium acetate buffer, is introduced into the binding chamber until a receptor concentration of $10^{-7}$ M is reached. As may be seen, this results in a decrease in EHNA signal as EHNA is taken up by the ADA. As the ADA becomes saturated with the EHNA, the 278 signal returns to its equilibrium value of about 10,000. At about 90 min, 25 µL of MeOH is again introduced to perturb binding and release of EHNA is observed. This peak is larger than the first peak at 10 min due to release from non-specific binding sites and from the ADA. As the MeOH passes through the chamber, and the buffer returns to binding conditions, the ADA again takes up EHNA. Again, at 135 min MeOH is introduced and again EHNA is released. This process is repeated a third time at about 180 min. In all three cases, EHNA is released after being bound to the ADA, demonstrating that the protein trapped in the chamber can bind and release ligand and in addition can be reused in additional binding experiments. At about 230 min the ADA is removed from the binding chamber by opening the binding chamber wash port 9. A subsequent injection of 25 µL MeOH at about 260 min results in release of EHNA of about the same magnitude as before the addition of ADA, confirming the original control at 10 min. These experiments demonstrate that a specific ligand can be extracted from solution onto a receptor, released for analysis, and the receptor reused for subsequent experiments.

EXAMPLE 4

Identification of an Adenosine Deaminase Inhibitor in a Library of Adenosine Analogs Screening of combinatorial libraries for compounds that bind to receptors such as adenosine deaminase are carried out in a manner similar to that described for the serum albumin Example 1. Calf intestinal adenosine deaminase (or another type of adenosine deaminase) is loaded into the molecular diversity screening device (equipped with a 10,000 molecular weight cutoff membrane) to a concentration of approximately 10 nM. A library of 20 adenosine analogs was prepared including the natural substrate for adenosine deaminase, adenosine (See list of compounds in Table 1).

TABLE 1

| Adenosine Deaminase Library | |
|---|---|
| EHNA | Hypoxanthine |
| Adenine | (−) Inosine |
| Adenosine | 5'-IMP |
| Adenine 9-α-D-arabinofuranoside | (−) 2'-Deoxyinoxine |

TABLE 1-continued

| Adenosine Deaminase Library | |
|---|---|
| EHNA | Hypoxanthine |
| 2'-AMP | 2'-Deoxyinosine 5'-monophosphate |
| 3'-AMP | Guanosine |
| 5'-AMP | Guanosine 5'-monophosphate |
| Adenosine 5'-carboxylic acid | Purine |
| ADP | Purine riboside |
| cAMP | Adenine $N^1$-oxide |

Figure 9:
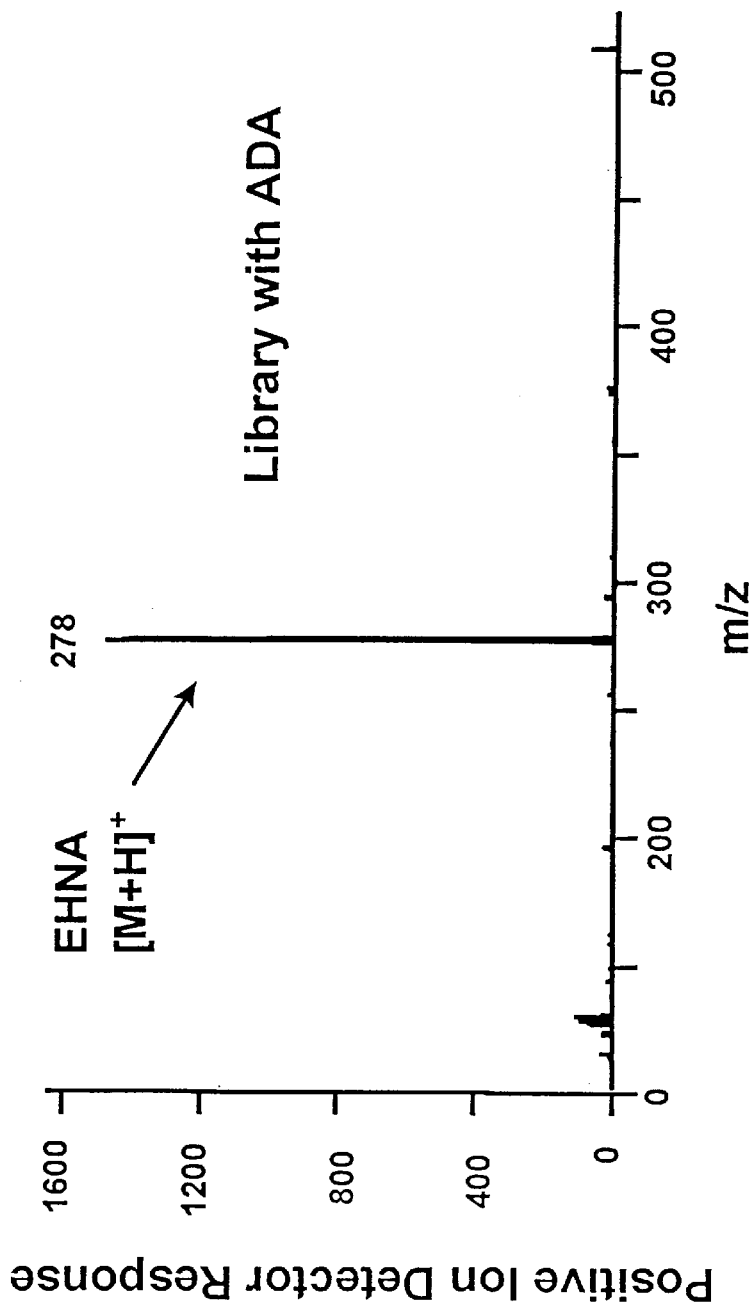
FIG. 9 is a graphical representation of the selection and release of EHNA from a library of chemical compounds.

A potent inhibitor of adenosine deaminase, EHNA (erythro-9-(2-hydroxy-3-nonyl)adenine, inhibitor dissociation constant equal to $2 \times 10^{-9}$ molar), was added to the library at 20-fold lower concentration than all other compounds. Next, the adenosine analog library was mixed with adenosine deaminase (in a 1:1 molar ratio) in 33 mM ammonium acetate buffer at pH 7.4, and an aliquot was injected into the molecular diversity screening device to achieve a concentration of adenosine deaminase of approximately 10 nM. After flushing the binding chamber with water at 100 µL/min for 12 min, to wash out library compounds with low affinity for adenosine deaminase, methanol/water (50:50) was pumped through the chamber at 50 µL/min. The latter procedure should perturb binding of any remaining compounds bound to the adenosine deaminase and release them into the detector. Using positive and negative ion electrospray mass spectrometry, only EHNA was detected ($[M+H]^+$ at m/z 278) eluting from the binding chamber (see FIG. 9). The small peaks at about 135 amu are due to fragment ions from the EHNA. Control experiments also show that all twenty of the library compounds were detectable by either positive or negative electrospray mass spectrometry. EHNA was identified in this library as the compound with the highest affinity for adenosine deaminase, therefore demonstrating the ability of the device and method to select from a series of related compounds that specific compound, i.e. EHNA, which binds to ADA with highest affinity.

EXAMPLE 5

Figure 10A:
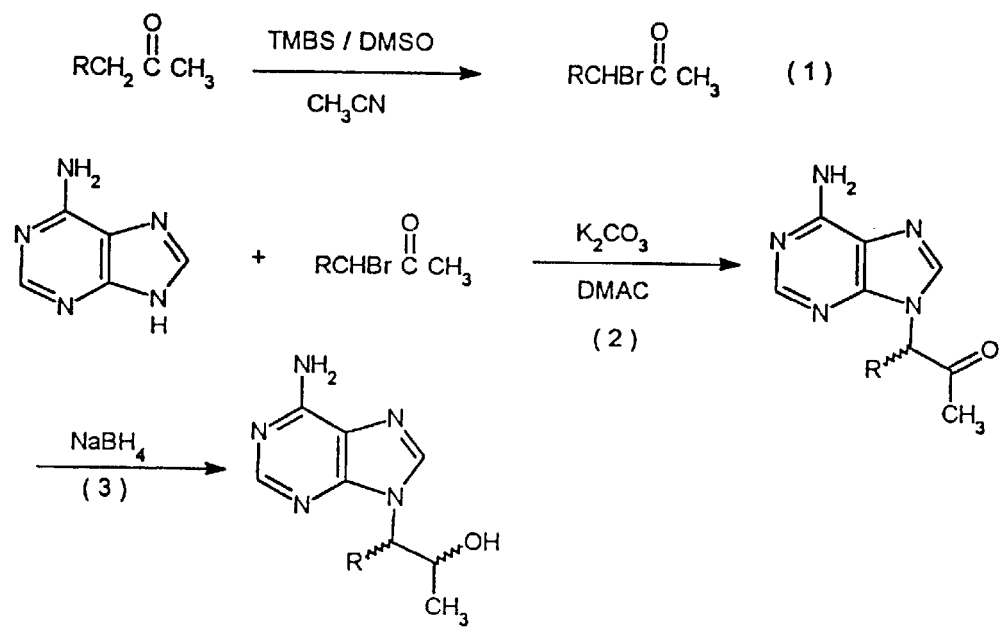
FIG. 10A shows a sequence of steps in that chemical synthesis of a 7-membered EHNA library.

Selective Identification of Adenosine Deaminase Inhibitors From a Synthetic Library of EHNA-type Analogs A family of seven EHNA-type analogs, potentially significant for co-administration with adenosine-type anti-tumor or anti-AIDS drugs to suppress their deactivation by adenosine deaminase, were synthesized as outlined in FIG. 10A. All three reactions were carried out without any attempt to isolate intermediate or final products. In addition to making multiple products by virtue of multiple reagents reacting at the same time, the chemistry outlined would be expected to produce many products due to side reactions. Thus, for each R group four isomers are expected about the two chiral centers in the molecule. Further, side reactions known to occur by virtue of alkylation of other nitrogens in the molecule and by virtue of unidentified other side reactions are expected.

Figure 10B:
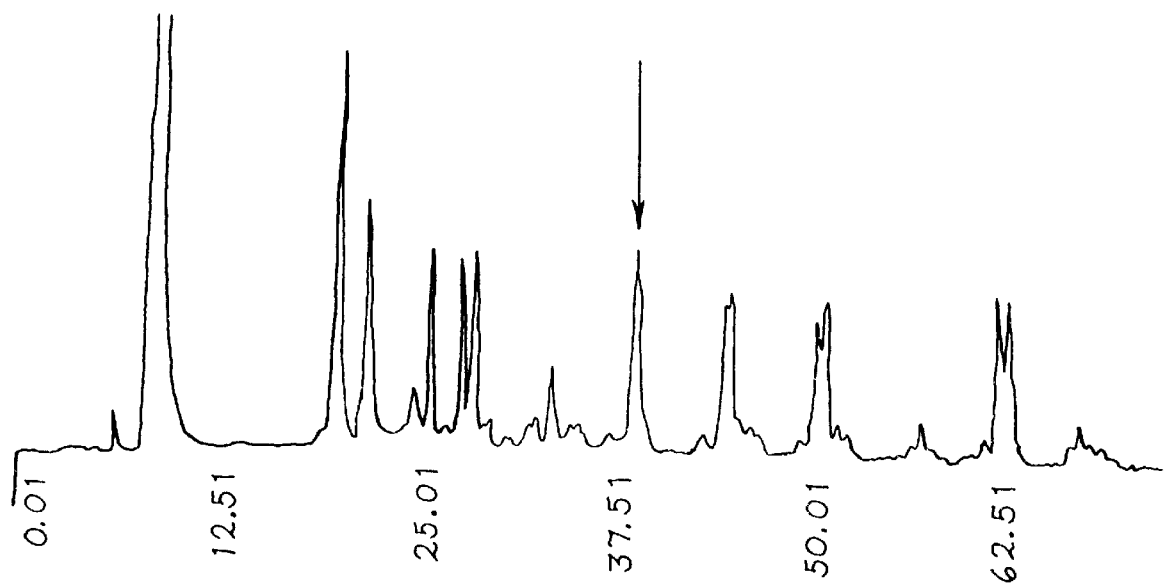
FIG. 10B is a reversed phase chromatographic profile of the products produced in the chemical synthesis.

To a stirred solution of a mixture of seven methyl ketones (1 mmol each, FIG. 10A) in 20 mL dry acetonitrile, were slowly added 8.8 mmol of trimethylbromosilane and then 8.8 mmol of dimethylsulfoxide. The reaction mixture was kept at room temperature for 2 hours before pouring the mixture into 80 mL water and extracting the mixture with ethyl ether (3×35 mL). The ether layer was dried over anhydrous sodium sulfate and taken to dryness in vacuo to give a brown residue. A stirred mixture of adenine (540 mg, 4 mmol), anhydrous potassium carbonate (552 mg, 4 mmol), and the brown residue containing the α-bromoketones from the first reaction (assumed 8 mmol) and N,N-dimethylacetamide (20 mL) were kept at 110° C. for 1 hr. After cooling, the reaction mixture was filtered and the filtrate was evaporated in vacuo to dryness. A mixture of NaBH$_4$ (610 mg, 16 mmol) and the brown solid obtained from this second reaction (assumed 8 mmol) in EtOH (25 mL) was allowed to stir at room temperature for 1 hr. The reaction was quenched by adding a small amount of acetic acid and the mixture was then neutralized with saturated aqueous NaHCO$_3$ and concentrated in vacuo. After dilution with water, the mixture was extracted with ethyl ether (3×10 mL). The ether layer was dried and evaporated in vacuo to get a brown residue which was subjected to reversed phase HPLC as show in FIG. 10b. As may be seen, numerous products are present in this reaction mixture. Co-chromatography of authentic EHNA, using LC/MS analysis showed that the peak indicated by the arrow in FIG. 10B was probably a mixture of the possible enantiomers and diastereomers of this molecule.

By using the methods and device described in this invention, this mixture of products was subjected to selective identification of those compounds in the mixture having affinity for adenosine deaminase. Calf intestinal adenosine deaminase was loaded into the molecular diversity screening device (equipped with a 10,000 molecular weight cutoff membrane) until a concentration of 7.35 μM (50 mM phosphate buffer) was reached. Next, the synthetic library of compounds to be assayed in phosphate buffer (50 mM) at pH 7.4 was injected into the binding chamber to achieve a concentration of approximately 10 nM for each analog. After flushing the chamber with water at 100 μL/min for 16 min, to wash out library compounds with low affinity for adenosine deaminase through the open waste valve, methanol/water (90:10 v/v) was pumped through the chamber at 50 μL/min to recover the bound adenosine deaminase compounds which were directed to the spectrometer with the waste valve closed. Using positive ion electrospray mass spectrometry in the scan mode, EHNA ([M+H]$^+$ at m/z 278) and two of its homologs (nC$_7$H$_{15}$, 306 and nC$_{10}$H$_{21}$, 334, see FIG. 9a for structures) were detected eluting from the device in the recovery phase. Ions corresponding to the isobutyl, the isobutylene and the benzylic derivatives were not detected in these scans when compared against appropriate controls, even though their presence in the reaction mixture before addition of protein was confirmed.

Figure 11B:
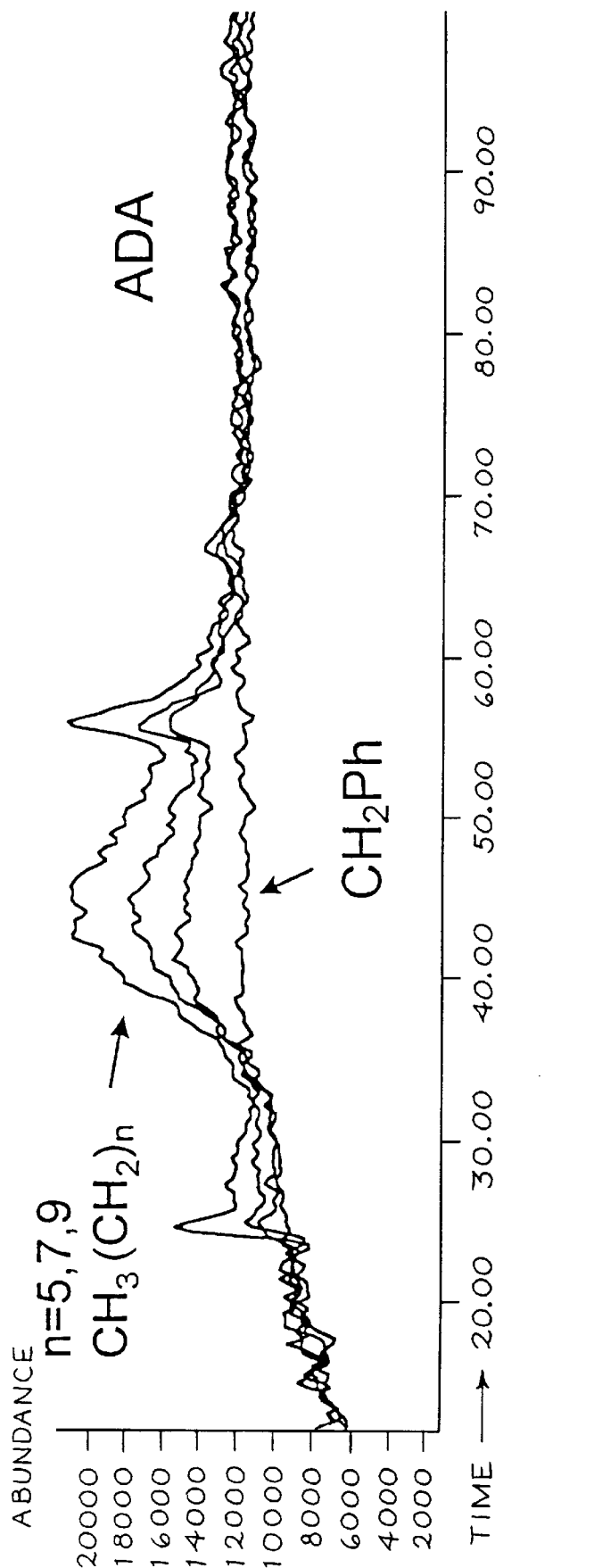
Figure 11C:
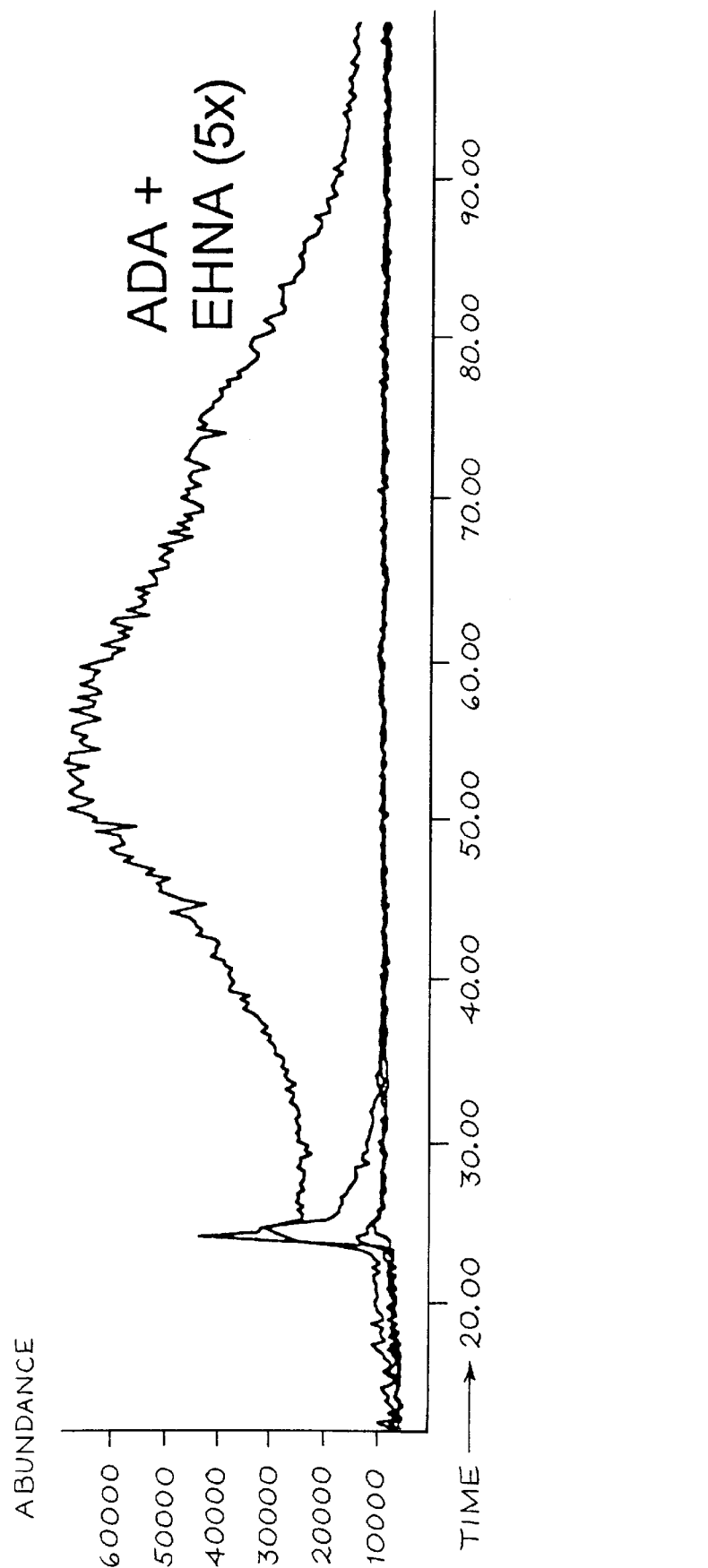

A similar series of experiments was conducted using positive ion electrospray mass spectrometry in the single ion monitoring mode. In these experiments ions for each of the seven EHNA-type analogs in the reaction mixture was monitored in the presence (FIG. 11B) and absence (FIG. 11A) of ADA and with a five-fold excess of authentic EHNA. The binding conditions were the same as in the scan mode with the aqueous MeOH being introduced at time zero on the X axis of the given diagrams in FIG. 11. As may be seen, in the absence of protein, compounds of the masses monitored are released by the MeOH at around 25 min (this corresponds to approximately the dead volume in the system). However, in the presence of ADA receptor molecules, masses corresponding to the normal alkanes n=5,7,9 (e.g. EHNA, n=5; see FIG. 10A for structures) are present. However, the isobutyl, isobutylene and benzylic derivatives did not appear in this region (only one of these, i.e. the benzylic derivative is presented for clarity). Further, in the presence of a five-fold excess of EHNA, the binding of the derivatives with m=7 and 9 are suppressed (FIG. 11C).

Thus, from a crude reaction mixture prepared in a few hours and containing many compounds, it was determined that only the alkane type derivatives of EHNA are probable targets for further investigation as inhibitors of ADA and as co-therapeutics for administration with adenosine type drugs.

EXAMPLE 6

Selection and Identification of Specific Compounds Which Bind to Collagenase With Affinities on the Order of $10^8$ Molar$^{-1}$ The enzymatic activity of collagenase appears to be important to the severity and the advancement of arthritis, and inhibitors of this and other metalloproteinases have potential therapeutic significance in this regard. A library of N-carboxyalkyl peptides, known to be inhibitors of collagenase, of the general structure:

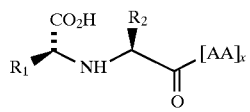

are prepared by the methods of Hagmann, W. K. et al. (1993), where R$_1$, R$_2$ and [AA]$_x$ are the same as those reported by this group. However, as with the synthesis of the EHNA analogs given in Example 5, the individual intermediate products are not isolated, and the precursor building blocks are added as mixtures. The crude reaction mixture from this series of reactions is then analyzed for binding in a manner similar to that described in Example 5. A buffered solution of collagenase is added to the binding chamber in the device described in FIGS. 2 and 3 to a final concentration of $10^{-6}$M. The crude synthetic reaction mixture is added to the collagenase in the binding chamber and the mixture allowed to incubate for several hours, at which time the chamber is flushed to waste and the waste valve closed. The bound compounds having affinity for the collagenase receptor are then released by acetonitrile into the spectrometer and subjected to MS/MS analyses. Structures are deduced by a combination of unit mass and MS/MS fragmentation analyses (some synthesis is necessary to resolve structural ambiguities). Structures of potential inhibitors so deduced are synthesized and characterized in the normal manner. The synthesized targets are then assayed for their inhibitory activity toward collagenase in the usual manner. It is to be recognized that such analysis typically does not constitute a rigorous structure activity relationship study, as some compounds may not be formed in sufficient quantity in the reaction to be detected. It only represents a rapid way to screen for potentially important leads.

EXAMPLE 7

Selection and Identification of Specific Compounds Which Bind to Collagenase With Affinities on the Order of $10^6$ Molar$^{-1}$ A similar set of experiments to that described in Example 6 is carried out with the binding chamber containing $10^{-4}$ molar collagenase. In the absence of higher affinity compounds, the products defined with the higher concentration of protein will identify compounds of lower affinity for the collagenase receptor than in Example 6.

EXAMPLE 8

Figure 12:
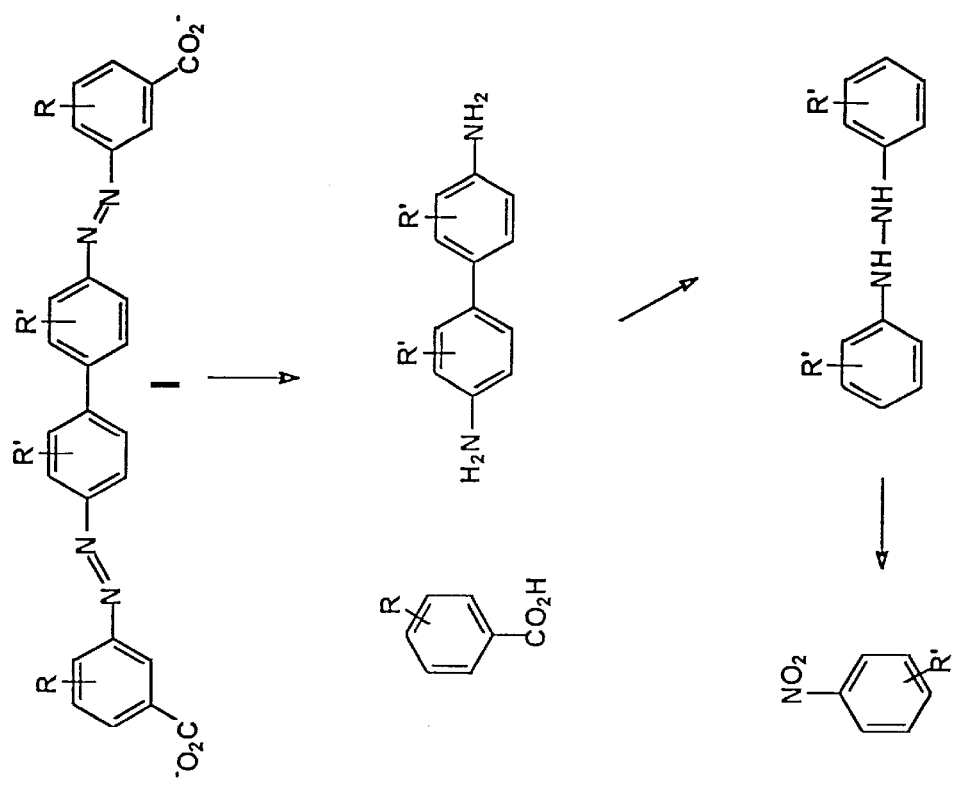
FIG. 12 is a retro-synthetic scheme for the synthesis of Congo Red analogs.

Selection and Identification of Specific Compounds Which Bind to β-Amyloid Peptide Carboxylic acid derivatives of Congo red (Klunk, et al., 1994) are known to bind to beta-amyloid deposits and are of potential use in inhibiting beta-amyloid deposition, a process thought to be responsible for neurological damage associated with Alzheimer's Disease. FIG. 12 outlines the retro-synthesis of a library of such derivatives using commercially available reagents in a "one pot" reaction leading to multiple combinations of reagents to give a combinatorial library of end products of the type I (FIG. 12, i.e. R=$nC_6H_{13}$; $nC_7H_{15}$; $nC_8H_{17}$; $nC_{10}H_{21}$; $(CH_3)_2CHCH_2$; $(CH_3)_2C=CHCH_2$; $PhCH_2$). The combinatorial library is assayed using the method and device of the invention described herein in a manner similar to Example 5. Thus, 83 $\mu$L of a micromolar suspension of commercially-available, synthetic beta-amyloid (Aβ(10–43)) is injected into the binding chamber, followed by a dilute solution of the synthetic combinatorial library containing about one receptor mole equivalent of each anticipated library compound. The chamber is washed with buffer to remove those library compounds not bound, or only weakly bound. The chamber is then washed with an aqueous methanol solution containing about three receptor mole equivalents of triethylamine in the recovery phase and the eluent products analyzed by mass spectrometry. Such compounds, having binding specificity for beta-amyloid aggregates are potential candidates for inhibiting beta-amyloid aggregation in vivo and thus for the treatment of Alzheimer's Disease.

EXAMPLE 9

Selective Identification of Peptides Which Bind to Renin

A buffered solution of commercially available renin (83 $\mu$L, $10^{-6}$M) is injected into the binding chamber. All possible natural peptides of length four residues (130,321 in number, ranging in mass from 246 to 762 AMU) are synthesized using split synthesis techniques, starting from both the carboxy terminus and the amino terminus (e.g. Salmon, et al., 1993). Thus, eight different pools of peptides are obtained. The relationship between the amino and carboxy synthesized pools (if the sequence of amino acid addition is the same in both cases) is that the pools synthesized from the amino terminus have the same amino acid at their carboxy end, while those synthesized from the carboxy terminus have the same amino acid at the amino end, and the sequence of all the peptides in the amino- and carboxy-terminus-paired pools have the reverse order. The pools are then assayed and the results of the carboxy-terminus-synthesized pools are compared against the amino-terminus-synthesized pools in a standard matrix format. One hundred mL of the synthetic mixtures containing approximately 100 pmoles of each peptide is eluted through the binding chamber at 100 $\mu$L/min over a period of about 16 hours with the waste valve 4 (FIG. 1) open. The binding chamber is then eluted with MeOH to disrupt the bound peptides which are analyzed as they elute into an ion trap mass spectrometer programmed to do ms/ms experiments. Ions present at a given Cartesian coordinate in the matrix, as previously discussed, define one or more possible peptide structures bound with affinity to the target renin. Subsequent analyses of the corresponding MS/MS fragmentation patterns provide unique peptide structures for peptides which bind renin with affinity. Such peptides having binding specificity for renin, or synthetic modifications thereof, are potential candidates for inhibiting renin function and thus for the treatment of hypertension.

It should be appreciated that the methods and apparatus of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

DOCUMENTS CITED

Chen, S. et al., "Pulsed Ultrafiltration Analysis of Compound/Macromolecule Interactions," *American Chemical Society Abstracts*, Chicago, Ill., August (1993)

Evans, G. K., et al., *Proc. Natl. Acad. Sci USA*, 86:5030 (1989)

Geysen, H. M. et al., *Proc Natl. Acad. Sci. USA*, 81:3998 (1984)

Hagmann, W. K. et al., *J. med. Chem.*, 36:4293–4301 (1993)

Klunk, W. et al., *Neurobio. Aging*, 15:691–698 (1994)

Lam et al., *Nature*, 354,82 (1991)

McGall et al., U.S. Pat. No. 5,412,087 (1995)

Moos, et al., *Ann. Rep. In Med. Chem.*, 28:315–324 (1993)

North, T. W. et al., *Pharmacol. Ther.* 4:81–108 (1979)

Pirrung, M. C., *J. Am. Chem. Soc.*, 117:1240 (1995)

Salmon, S. E. et al., *Proc. Natl. Acad. Sci. USA*, 90:11708 (1993)

Smith, G. P., *Science*, 228:1315 (1985)

Smith, P. W. et al., *Bioorg. Med. Chem. Lett.*, 4:2821 (1994)

Stryer, et al., *Science*, 251:767–773 (1991)

Woodbury, et al., *Anal. Chem.*, 67:885–890 (1995)

What is claimed:

1. A method for identifying a chemical compound present in a mixture of compounds in solution, said identifying determined by the ability of the compound to bind to a predetermined target macromolecule in solution, said method comprising:
    a) contacting the mixture of compounds to the target macromolecule in solution under conditions that allow a compound having binding affinity for the target macromolecule to become a bound compound, said contacting taking place on a binding side of an ultrafiltration membrane in an ultrafiltration device;
    b) separating non-bound compounds from the bound compound by passing the non-bound compounds through the ultrafiltration membrane and discarding the non-bound compounds;
    c) releasing the bound compound from the macromolecule wherein the macromolecule remains in solution for reuse on the binding side of the ultrafiltration membrane, and wherein the released compound passes through the ultrafiltration membrane; and
    d) identifying the released compound after it passes through the ultrafiltration membrane, said identifying taking place in real time.

2. The method of claim 1, wherein contacting of the mixture of compounds to the macromolecule is by means of an injection.

3. The method of claim 2, wherein the injection is a pulse.

4. The method of claim 1, wherein said identifying of the released compound in real time is performed with a mass spectrometer coupled to an outlet port of said ultrafiltration device.

* * * * *